(12) United States Patent
O'Donnell et al.

(10) Patent No.: US 10,345,267 B2
(45) Date of Patent: Jul. 9, 2019

(54) COMPOSITE INSPECTION

(71) Applicants: The Boeing Company, Chicago, IL (US); University of Washington, Seattle, WA (US)

(72) Inventors: Matthew O'Donnell, Seattle, WA (US); Ivan Pelivanov, Seattle, WA (US); Steven Kenneth Brady, Renton, WA (US); Gary Ernest Georgeson, Tacoma, WA (US); Jeffrey Reyner Kollgaard, Seattle, WA (US); William P. Motzer, Charleston, SC (US); Clarence Lavere Gordon, III, Renton, WA (US); Jill Paisley Bingham, Seattle, WA (US); Alan F. Stewart, Seattle, WA (US); James C. Kennedy, Summerville, SC (US)

(73) Assignee: The Boeing Company, Chicago, IL (US)

( * ) Notice: Subject to any disclaimer, the term of this patent is extended or adjusted under 35 U.S.C. 154(b) by 334 days.

(21) Appl. No.: 15/070,261

(22) Filed: Mar. 15, 2016

(65) Prior Publication Data

US 2017/0176393 A1    Jun. 22, 2017

Related U.S. Application Data

(60) Provisional application No. 62/270,529, filed on Dec. 21, 2015.

(51) Int. Cl.
*G01N 29/06* (2006.01)
*G01N 21/17* (2006.01)
(Continued)

(52) U.S. Cl.
CPC .......... *G01N 29/0645* (2013.01); *B64F 5/60* (2017.01); *G01N 21/1702* (2013.01);
(Continued)

(58) Field of Classification Search
CPC .......... G01N 21/1702; G01N 29/0645; G01N 29/043; G01N 29/4454; G01N 29/46; G01N 2291/2694; A61B 5/0095
See application file for complete search history.

(56) References Cited

U.S. PATENT DOCUMENTS

| 5,010,885 A | 4/1991 | Fink et al. |
| 6,200,266 B1 * | 3/2001 | Shokrollahi ........ G01S 7/52036 |
| | | 600/438 |

(Continued)

FOREIGN PATENT DOCUMENTS

| CA | 2314305 A1 | 7/2000 |
| JP | 2011058937 A1 | 3/2011 |

OTHER PUBLICATIONS

Extended European Search Report, dated Feb. 6, 2017, regarding Application No. 16192874.2, 10 pages.
(Continued)

*Primary Examiner* — Maurice C Smith
(74) *Attorney, Agent, or Firm* — Yee & Associates, P.C.

(57) ABSTRACT

A method of detecting material changes in a composite structure is presented. A pulsed laser beam is directed towards the composite structure comprised of a number of composite materials. Wide-band ultrasonic signals are formed in the composite structure when radiation of the pulsed laser beam is absorbed by the composite structure. The wide-band ultrasonic signals are detected to form data. The data comprises a number of ultrasonic A-scans. The data is processed to identify a plurality of frequency measurements for each of the number of ultrasonic A-scans. A frequency image is displayed using the plurality of frequency measurements. The material changes are represented in the frequency image.

21 Claims, 12 Drawing Sheets

(51) Int. Cl.
- *G01N 29/24* (2006.01)
- *G01N 29/04* (2006.01)
- *G01N 29/11* (2006.01)
- *G01N 29/34* (2006.01)
- *G01N 29/44* (2006.01)
- *G01N 29/46* (2006.01)
- *G01N 29/50* (2006.01)
- *B64F 5/60* (2017.01)

(52) U.S. Cl.
CPC ........... *G01N 29/043* (2013.01); *G01N 29/11* (2013.01); *G01N 29/2418* (2013.01); *G01N 29/343* (2013.01); *G01N 29/348* (2013.01); *G01N 29/449* (2013.01); *G01N 29/4454* (2013.01); *G01N 29/46* (2013.01); *G01N 29/50* (2013.01); *G01N 2021/1706* (2013.01); *G01N 2291/015* (2013.01); *G01N 2291/0231* (2013.01); *G01N 2291/044* (2013.01); *G01N 2291/2694* (2013.01)

(56) References Cited

U.S. PATENT DOCUMENTS

| | | | |
|---|---|---|---|
| 8,814,794 B2 * | 8/2014 | Oishi | A61B 6/56 600/437 |
| 9,164,066 B1 | 10/2015 | Bossi et al. | |
| 9,188,566 B2 | 11/2015 | Georgeson et al. | |
| 9,250,213 B1 | 2/2016 | Bossi et al. | |
| 2005/0177310 A1 * | 8/2005 | Duncan | G01V 11/002 702/14 |
| 2010/0070233 A1 * | 3/2010 | Masumura | A61B 5/0091 702/127 |
| 2011/0119011 A1 * | 5/2011 | Yamazoe | G01B 11/2441 702/85 |
| 2013/0088724 A1 | 4/2013 | DuBois et al. | |
| 2013/0281819 A1 * | 10/2013 | Schmid | A61B 5/0095 600/407 |
| 2013/0289381 A1 * | 10/2013 | Oraevsky | A61B 5/7425 600/407 |
| 2013/0311110 A1 * | 11/2013 | Aizikov | H01J 49/0036 702/32 |
| 2014/0116146 A1 | 5/2014 | Bossi et al. | |
| 2014/0230556 A1 * | 8/2014 | Yamamoto | G01N 29/069 73/602 |
| 2015/0168352 A1 * | 6/2015 | Sohn | F03D 17/00 73/643 |
| 2015/0300995 A1 | 10/2015 | Flynn et al. | |
| 2016/0109332 A1 * | 4/2016 | Araki | G01B 11/2522 702/167 |

OTHER PUBLICATIONS

Pelivanov et al., "Heat damage evaluation in carbon fiber-reinforced composites with kHz A-scan rate fiber-optic pump-probe laser-ultrasound system", Elsevier Ltd., © 2016, 11 pages.

Bossi et al., "Ultrasound Inspection System for Inspecting a Test Object with Non-Planar Features," U.S. Appl. No. 13/526,853, filed Jun. 19, 2012, 62 pages.

Pelivanov et al., "A kHz rate pump-probe scanner for advanced evaluation of aircraft composites," International Symposium on Laser Ultrasonics and Advanced Sensing, paper No. 12, Jun. 2015, 3 pages.

Pelivanov et al., "A new fiber-optic non-contact compact laser-ultrasound scanner for fast non-destructive testing and evaluation of aircraft composites," Journal of Applied Physics, vol. 115, Mar. 2014, 12 pages.

Pelivanov et al., "NDT of fiber-reinforced composites with a new fiber-optic pump-probe laser-ultrasound system," Photoacoustics, vol. 2, Jan. 2014, 13 pages.

* cited by examiner

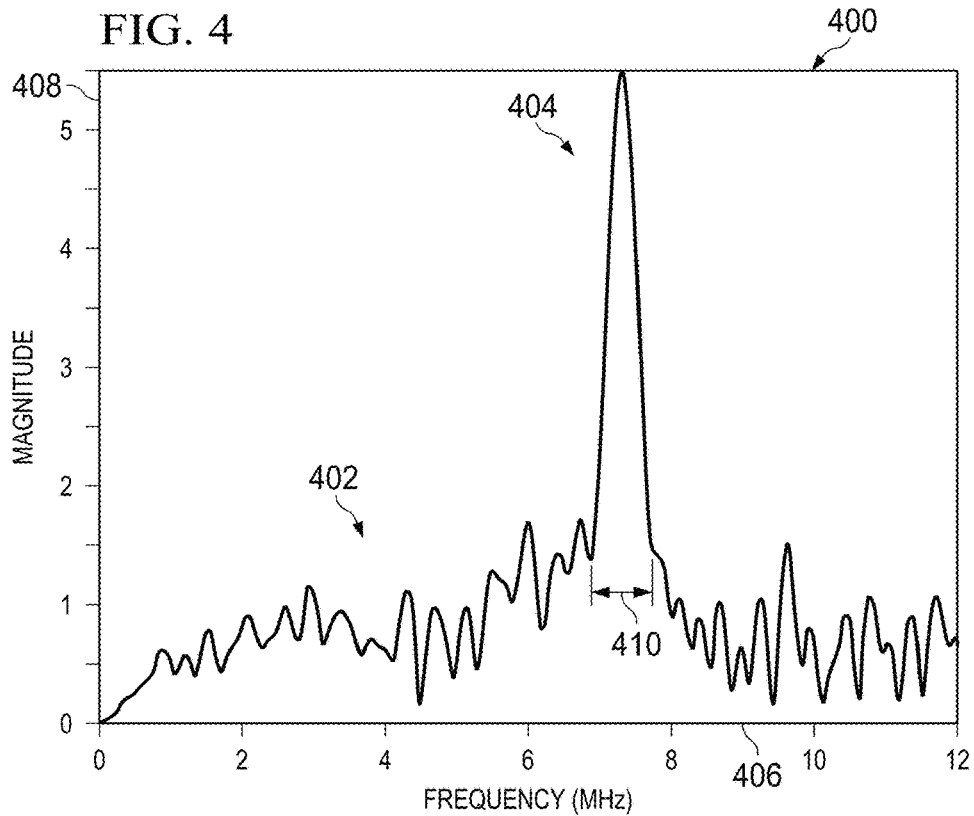
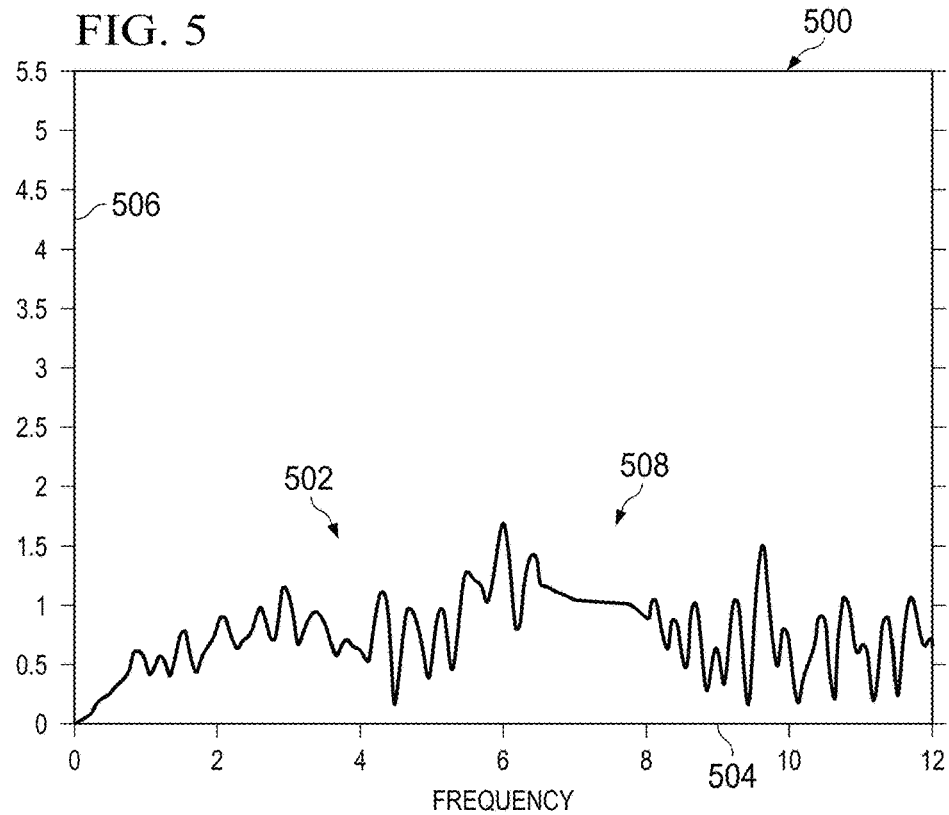

COMPOSITE INSPECTION

RELATED PROVISIONAL APPLICATION

This application claims the benefit of U.S. Provisional Patent Application Ser. No. 62/270,529, filed Dec. 21, 2015, and entitled "Composite Inspection."

BACKGROUND INFORMATION

1. Field

The present disclosure relates generally to non-destructive inspection and, in particular, to performing non-destructive inspection on a layered structure. Still more particularly, the present disclosure relates to a method and apparatus for detecting material changes or other inconsistencies in a composite structure.

2. Background

In manufacturing aircraft, vehicles, and other structures, inspection of parts used to form these structures is often performed to determine whether the parts will have desired parameters for a desired performance of the part. Additionally, the structures and parts are inspected as part of normal maintenance when the aircraft, vehicles, and other structures are in use.

Non-destructive testing is commonly performed on these parts. Non-destructive testing is used to evaluate the properties of a part without altering the ability to use the part in service.

Ultrasound testing is a type of non-destructive testing. Ultrasound testing is often used to perform inspections on aircraft parts that include, or are comprised of, composite materials. Ultrasound testing involves transmitting sound waves through a test object, such as an aircraft part or structure.

Ultrasound testing is commonly performed using a transducer. The transducer is configured to send sound waves into a test object and detect a response to the sound waves. The response to these sound waves is analyzed to determine whether inconsistencies are present in the test object.

Aircraft, cars, medical devices, and even clothing are being designed and manufactured with greater and greater percentages of composite materials. For example, composite materials are used in aircraft to decrease the weight of the aircraft. This decreased weight improves performance features such as payload capacity and fuel efficiency. Further, composite materials provide longer service life for various components in an aircraft. Composite materials may also decrease the weight of other items such as artificial limbs, bicycles, cars, body armor, or other desirable products.

Composite materials may be tough, light-weight materials created by combining two or more functional components. For example, a composite material may include reinforcing fibers bound in a polymer resin matrix. Resins used in composite materials may include thermoplastic or thermoset resins. The fibers may be unidirectional or may take the form of a woven cloth or fabric.

In manufacturing composite structures, layers of composite material are typically laid up on a tool. The layers may be comprised of fibers in sheets. These sheets may take the form of fabrics, tape, tows, or other suitable forms. In some cases, resin may be infused or preimpregnated into the sheets. These types of sheets are commonly referred to as prepreg. The different layers of prepreg may be laid up in different orientations, and different numbers of layers may be used depending on the performance requirements of the composite structure being manufactured.

Inconsistencies may be introduced to the composite structure during manufacturing or during use of the composite structure. Due to the regular spacing of the layers that make up the composite material, inspection of the composite material may be more difficult than desired for some locations or some types of inconsistencies.

Further, some inconsistencies may not be conventionally detectable using conventional non-destructive techniques. Therefore, it would be desirable to have a method and apparatus that take into account at least some of the issues discussed above, as well as other possible issues.

SUMMARY

In one illustrative embodiment, a method of detecting material changes in a composite structure is presented. A pulsed laser beam is directed towards the composite structure comprised of a number of composite materials. Wide-band ultrasonic signals are formed in the composite structure when radiation of the pulsed laser beam is absorbed by the composite structure. The wide-band ultrasonic signals are detected to form data. The data comprises a number of ultrasonic A-scans. The data are processed to identify a plurality of frequency measurements for each of the number of ultrasonic A-scans. A frequency image is displayed using the plurality of frequency measurements. The material changes are represented in the frequency image.

In another illustrative embodiment, a method is presented. A pulsed laser beam is directed towards a composite structure comprised of a plurality of layers. A number of wide-band ultrasonic signals are formed in the composite structure when radiation of the pulsed laser beam is absorbed by the composite structure. The wide-band ultrasonic signals are detected to form data. The data comprises a plurality of ultrasonic A-scans for the composite structure. A moving window is applied to each of the plurality of ultrasonic A-scans to form windowed signals. A frequency measurement is determined within the windowed signals for each of the plurality of ultrasonic A-scans. Spectral components of a structure signal are removed from an A-scan spectrum of each of the plurality of ultrasonic A-scans using the frequency measurement. An interpolation is performed on the A-scan spectrum of the each of the plurality of ultrasonic A-scans after removing the spectral components of the structure signal to form interpolated A-scan spectrum data.

In a further illustrative embodiment, a method is presented. Data for a composite structure are obtained using a laser ultrasound inspection system. A frequency and a width of spectral components of a structure signal in the data are determined. The spectral components of the structure signal are removed from the data in a frequency domain. An interpolation routine is performed to fill in a region of an A-scan spectrum left empty by removing the spectral components of the structure signal to form interpolated data. An inverse Fourier transformation is performed on the interpolated data to form a processed A-scan with the structure signal removed.

The features and functions can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the illustrative embodiments are set forth in the appended claims. The illustrative embodiments, however, as well as a preferred mode of use, further objectives and features thereof, will best be understood by reference to the following detailed description of an illustrative embodiment of the present disclosure when read in conjunction with the accompanying drawings, wherein:

FIG. 4 is an illustration of an ultrasonic A-scan spectrum in the frequency domain in accordance with an illustrative embodiment;

FIG. 5 is an illustration of an interpolated ultrasonic A-scan spectrum in the frequency domain in accordance with an illustrative embodiment;

DETAILED DESCRIPTION

The different illustrative embodiments recognize and take into account one or more different considerations. For example, the illustrative embodiments recognize and take into account that the performance of composite structures depend on both composition and fabrication quality. The illustrative embodiments further recognize and take into account that the structural properties of composite materials may be sensitive to irreversible chemical and mechanical degradation following stresses. The stresses may be thermal or mechanical. For example, thermal stresses may be placed on composite materials by lightning strikes, jet engine exhaust, fires, or other thermal incidences.

The illustrative embodiments recognize and take into account that thermal or mechanical stresses may cause material changes in the composite structure. These material changes may reduce the strength of the composite structure. The illustrative embodiments further recognize and take into account that composite materials may have reduced strength without any evident inconsistencies.

The illustrative embodiments recognize and take into account that conventional ultrasound and x-ray inspections may detect macroscopic flaws in composite materials. However, the illustrative embodiments also recognize and take into account that conventional ultrasound and x-ray inspections do not detect stress-induced material changes in a composite structure. The illustrative embodiments recognize and take into account that conventional inspection techniques that detect material changes may be limited to surface changes. Currently, no conventional inspection technique may evaluate the full composite material volume for stress-induced material changes.

Figure 1:
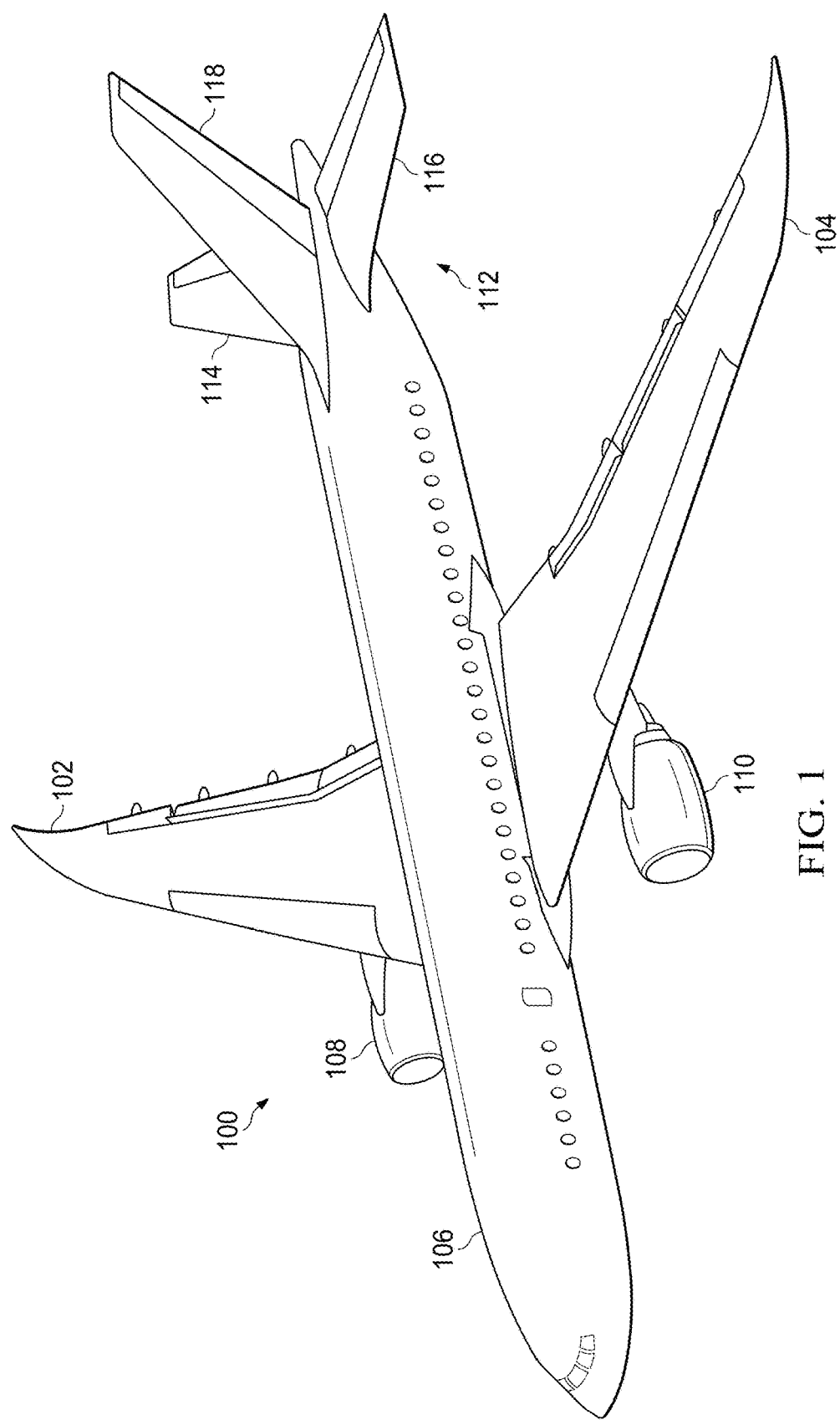
FIG. 1 is an illustration of an aircraft in which an illustrative embodiment may be implemented.

With reference now to the figures, and in particular, with reference to FIG. 1, an illustration of an aircraft is depicted in which an illustrative embodiment may be implemented. In this illustrative example, aircraft 100 has wing 102 and wing 104 attached to body 106. Aircraft 100 includes engine 108 attached to wing 102 and engine 110 attached to wing 104.

Body 106 has tail section 112. Horizontal stabilizer 114, horizontal stabilizer 116, and vertical stabilizer 118 are attached to tail section 112 of body 106.

Aircraft 100 is an example of an aircraft having composite structures that may be inspected with a laser ultrasound inspection system in accordance with an illustrative embodiment. For example, composite skin in at least one of wing 102 or wing 104 may be inspected using a laser ultrasound inspection system.

As used herein, the phrase "at least one of," when used with a list of items, means different combinations of one or more of the listed items may be used, and only one of each item in the list may be needed. In other words, "at least one of" means any combination of items and number of items may be used from the list, but not all of the items in the list are required. The item may be a particular object, thing, or a category.

For example, "at least one of item A, item B, or item C" may include, without limitation, item A, item A and item B, or item B. This example also may include item A, item B, and item C or item B and item C. Of course, any combinations of these items may be present. In other examples, "at least one of" may be, for example, without limitation, two of item A; one of item B; and ten of item C; four of item B and seven of item C; or other suitable combinations.

This illustration of aircraft 100 is provided for purposes of illustrating one environment in which the different illustrative embodiments may be implemented. The illustration of aircraft 100 in FIG. 1 is not meant to imply architectural limitations as to the manner in which different illustrative embodiments may be implemented. For example, aircraft 100 is shown as a commercial passenger aircraft. The different illustrative embodiments may be applied to other types of aircraft, such as a private passenger aircraft, a rotorcraft, or other suitable types of aircraft.

Although the illustrative examples for an illustrative embodiment are described with respect to an aircraft, an illustrative embodiment may be applied to other types of platforms. The platform may be, for example, a mobile platform, a stationary platform, a land-based structure, an aquatic-based structure, or a space-based structure. More specifically, the platform may be a surface ship, a tank, a personnel carrier, a train, a spacecraft, a space station, a satellite, a submarine, an automobile, a manufacturing facility, a building, or other suitable platforms.

Further, an illustrative embodiment may be applied to other types of composite structures. For example, composite structures other than platforms may be inspected for material changes using a laser ultrasound inspection system. Composite structures other than platforms may include medical devices, prosthetic limbs, or any other desirable products for the screening, diagnosis, treatment, or prevention or any combination or sub-combination thereof of physical or mental health conditions in human beings or animals.

Figure 2:
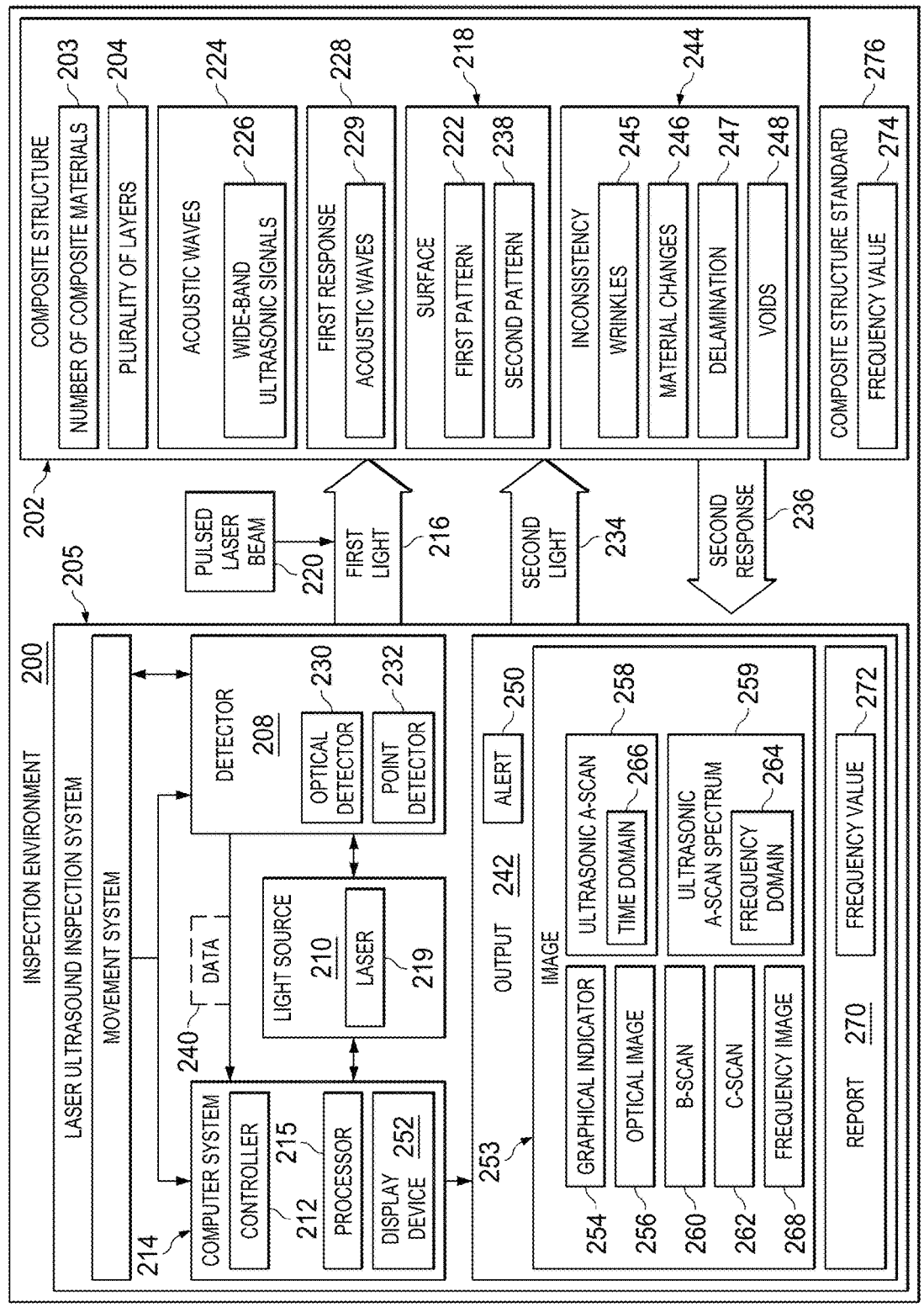
FIG. 2 is an illustration of a block diagram of an inspection environment in accordance with an illustrative embodiment.

With reference now to FIG. 2, an illustration of a block diagram of an inspection environment is depicted in accordance with an illustrative embodiment. As depicted, inspection environment 200 includes composite structure 202. Composite structure 202 may take any number of forms. For example, composite structure 202 may be a part for an aircraft. Composite structure 202 is comprised of number of composite materials 203. Further, composite structure 202 is formed of plurality of layers 204. In some illustrative examples, plurality of layers 204 has a substantially consistent thickness and spacing.

In these illustrative examples, composite structure 202 is a composite part for an aircraft selected from one of a panel, a fuselage barrel, a stringer, a spar, a rib, a wing box, a wing, a stabilizer, and other suitable types of parts. Composite structure 202 is inspected using laser ultrasound inspection system 205. As depicted, laser ultrasound inspection system 205 includes movement system 206, detector 208, light source 210, and controller 212.

In these illustrative examples, controller 212 controls the operation of laser ultrasound inspection system 205. Controller 212 may be implemented using hardware, software, firmware, or a combination thereof.

In these illustrative examples, controller 212 may be implemented within computer system 214. Computer system 214 may be one or more computers. When more than one computer is present in computer system 214, those computers may be in communication with each other through a communications medium such as a network.

When software is used, the operations performed by the controller may be implemented using, for example, without limitation, program code configured to run on a processor unit, such as processor 215. When firmware is used, the operations performed by the controller may be implemented using, for example, without limitation, program code and data and stored in persistent memory to run on a processor unit.

When hardware is employed, the hardware may include one or more circuits that operate to perform the operations performed by the controller. Depending on the implementation, the hardware may take the form of a circuit system, an integrated circuit, an application specific integrated circuit (ASIC), a programmable logic device, or some other suitable type of hardware device configured to perform any number of operations.

A programmable logic device may be configured to perform certain operations. The device may be permanently configured to perform these operations or may be reconfigurable. A programmable logic device may take the form of, for example, without limitation, a programmable logic array, a programmable array logic, a field programmable logic array, a field programmable gate array, or some other type of programmable hardware device.

In some illustrative examples, the operations and/or processes performed by the controller may be performed using organic components integrated with inorganic components. In some cases, the operations and/or processes may be performed by entirely organic components, excluding a human being. As one illustrative example, circuits in organic semiconductors may be used to perform these operations and/or processes.

Movement system 206 is configured to move light source 210 and detector 208 relative to composite structure 202. Movement system 206 may be implemented using a number of different types of systems. In one example, movement system 206 is a robot. The robot may be, for example, a robotic arm that may move detector 208 about a number of axes. Movement system 206 also may be, for example, without limitation, a gantry robot, a hand-operated scanning head, and other suitable types of movement systems.

Light source 210 is configured to transmit first light 216 onto surface 218 of composite structure 202. In some illustrative examples, light source 210 is be laser 219. In one specific example, laser 219 is a diode-pumped nanosecond laser. When light source 210 takes the form of laser 219, first light 216 may be pulsed laser beam 220.

In this illustrative example, first light 216 is transmitted in a manner that forms first pattern 222 on surface 218 of composite structure 202. In these illustrative examples, first pattern 222 of first light 216 is a plurality of areas on which first light 216 illuminates on surface 218. These areas may be circular, oval, square, oblique, or have some other shape depending on the angle of projection onto the surface. In some illustrative examples, first pattern 222 takes the form of a line.

First light 216 is configured to generate acoustic waves 224 within composite structure 202 when first light 216 encounters composite structure 202. Acoustic waves 224 occur when first light 216 is transmitted onto surface 218 of composite structure 202. For example, energy in first light 216 causes thermoelastic expansion in composite structure 202. The thermoelastic expansion results in acoustic waves 224 in composite structure 202.

In these illustrative examples, acoustic waves 224 are ultrasound waves. Thus, acoustic waves 224 are ultrasonic signals. More specifically, acoustic waves 224 take the form of wide-band ultrasonic signals 226. Wide-band ultrasonic signals 226 may have bandwidth greater than or equal to 50%. In these examples, the range of frequencies in a pulse is >=50% of the characteristic frequency of the pulse.

Acoustic waves 224 may have, for example, a frequency from about 20 kilohertz to about 100 megahertz depending on the particular implementation. The frequency for acoustic waves 224 depends on the material used to form composite structure 202, the pulse width of the laser excitation, and other suitable factors.

Additionally, detector 208 is configured to detect first response 228 to acoustic waves 224. First response 228 includes acoustic waves 229 that may occur as a result of scattering, reflection, modulation, and other changes to acoustic waves 224 traveling within composite structure 202. First response 228 is comprised of acoustic waves 229 that occur in response to acoustic waves 224. In this illustrative example, first response 228 is detected by detector 208.

In some illustrative examples, detector 208 takes the form of optical detector 230. In some illustrative examples, detector 208 is point detector 232. In one example, detector 208 may comprise any form of interferometer. For example, detector 208 includes a fiber-optic modified Sagnac interferometer for non-contact detection of backscattered ultrasound. Detector 208 transmits second light 234 onto surface 218 of composite structure 202 and detects second response 236 to second light 234.

In one illustrative example, second light 234 is transmitted in the form of second pattern 238 onto surface 218 of composite structure 202. In this illustrative example, second pattern 238 takes the form of a point.

Second response 236 is second light 234 that has been deflected by first response 228 in this illustrative example. First response 228, caused by acoustic waves 224 traveling within composite structure 202, reaches surface 218 and is detected. In some illustrative examples, the detection of first response 228 is detected using an interferometer that sends a reference light, such as second light 234 and detects the mechanical vibrations on surface 218 in second response 236. Detector 208 includes any desirable form of interferometer.

Detector 208 sends data 240 to controller 212 when second response 236 is detected. Data 240 is used by controller 212 to generate output 242. In some examples, data 240 includes a full-bandwidth signal for a location of composite structure 202 being inspected. When data 240 includes received signals for a plurality of locations of composite structure 202, data 240 includes a plurality of ultrasonic A-scans. As laser ultrasound inspection system 205 is scanned across composite structure 202, data 240 for a plurality of locations on composite structure 202 is collected.

As depicted, output 242 indicates whether inconsistency 244 is present in composite structure 202. Inconsistency 244 may be, for example, without limitation, wrinkles 245, material changes 246, delamination 247, voids 248, and other undesired features or properties in composite structure 202. In some illustrative examples, material changes 246 may be referred to as "local." Local material changes 246 refer to inconsistency 244 in an area of composite structure 202 that has been inspected using laser ultrasound inspection system 205. Material changes 246 result from at least one of thermal stresses or physical stresses on composite structure 202 prior to directing pulsed laser beam 220 towards the composite structure 202.

Output 242 takes any desirable form. For example, output 242 may take the form of alert 250. Alert 250 indicates whether inconsistency 244 is present. Alert 250 may be displayed on display device 252 within computer system 214.

In another illustrative example, output 242 is image 253. Image 253 also may be displayed on display device 252. In one illustrative example, image 253 is an image of a portion or all of composite structure 202 with graphical indicator 254 when inconsistency 244 is present in composite structure 202. In one example, Graphical indicator 254 is displayed in a location in image 253 corresponding to a location in composite structure 202 where inconsistency 244 is detected. In other illustrative examples, if inconsistency 244 is absent, graphical indicator 254 may be displayed to indicate an absence of inconsistency 244.

In some illustrative examples, image 253 is optical image 256. Optical image 256 may be an image of surface 218 of composite structure 202.

In other illustrative examples, image 253 is a representation of a portion of composite structure 202. For example, image 253 is selected from ultrasonic A-scan 258, ultrasonic A-scan spectrum 259, B-scan 260, or C-scan 262. Ultrasonic A-scan 258 and ultrasonic A-scan spectrum 259 may each be a graph. Ultrasonic A-scan spectrum 259 is displayed in frequency domain 264. Ultrasonic A-scan spectrum 259 is computed by Fourier transform of ultrasonic A-scan 258. Ultrasonic A-scan 258 is in time domain 266. Ultrasonic A-scan 258 in time domain 266 is obtained by performing an inverse Fourier transform on ultrasonic A-scan spectrum 259 in frequency domain 264. In one example, frequency domain 264 has an x-axis of frequency and a y-axis of amplitude. In one example, time domain 266 has an x-axis of time and a y-axis of amplitude.

In some illustrative examples, ultrasonic A-scan 258 may be a representation of data 240. As a result, data 240 may be said to include ultrasonic A-scan 258. In other illustrative examples, ultrasonic A-scan 258 may be a representation of a portion of data 240 after data 240 is processed.

Ultrasonic A-scan 258 is representative of a location of composite structure 202. Data from ultrasonic A-scan 258 is combined with data from a plurality of ultrasonic A-scans of different locations of composite structure 202 to form B-scan 260. B-scan 260 may be at least one of a color or a grayscale image. The value of each pixel in B-scan 260 is representative of an intensity of second response 236 of a corresponding location of composite structure 202.

In one example, B-scan 260 has an x-axis of scanning distance and a y-axis of time. B-scan 260 may be a representation of data 240 or a representation of data 240 after data 240 is processed.

C-scan 262 is representative of all or a portion of composite structure 202. In one example, C-scan 262 has the same two-dimensional shape as all or a portion of composite structure 202. In some illustrative examples, C-scan 262 is a grayscale image. In other illustrative examples, C-scan 262 is a color image. The value of each pixel in C-scan 262 is representative of any desirable information. In one example, the value of each pixel in C-scan 262 is representative of locations of inconsistency 244 in composite structure 202. More specifically, the value of each pixel in C-scan 262 may be representative of locations of material changes 246 in composite structure 202.

In another illustrative example, image 253 takes the form of frequency image 268. Frequency image 268 is similar to B-scan 260 or to C-Scan 262 in the x-axis and y-axis types. For example, frequency image 268 may have an x-axis of scanning distance and a y-axis of time. However, the intensity of each pixel in frequency image 268 is indicative of a frequency such as a mean frequency or a max frequency determined by processing data 240. Frequency image 268 indicates the presence of material changes 246 in a portion of composite structure 202 represented in frequency image 268.

In still another illustrative example, output 242 takes the form of report 270. Report 270 may identify any inconsistencies in composite structure 202. Report 270 also may include other information, such as locations of inconsistencies, types of inconsistencies, sizes of inconsistencies, and other suitable types of information.

In some illustrative examples, report 270 includes frequency value 272. Frequency value 272 is an average of mean frequencies or maximum frequencies for a portion of composite structure 202 or for all locations of composite structure 202 inspected using laser ultrasound inspection system 205. The sample volume of composite structure 202 to average for frequency value 272 is determined by at least one of the initial material properties, scale of inhomogeneities to detect, accuracy of measurements, or other characteristics. Frequency value 272 is representative of the presence or absence of material changes 246 in composite structure 202. Frequency value 272 may be referred to as "local." Local frequency value 272 is an average of local values of mean frequencies or maximum frequencies determined for a certain volume of material in which the local material changes 246 are to be determined.

In one example, frequency value 272 is compared to frequency value 274 of composite structure standard 276. Composite structure standard 276 has the same layup and materials as composite structure 202. Composite structure standard 276 is verified to have desirable structural properties. When frequency value 272 differs from frequency value 274 of composite structure standard 276, frequency value 272 may indicate material changes 246 in composite structure 202. Thus, output 242 may be at least one of alert 250, image 253, report 270, or other suitable types of output.

The illustration of manufacturing environment 200 in FIG. 2 is not meant to imply physical or architectural limitations to the manner in which an illustrative embodiment may be implemented. Other components in addition to or in place of the ones illustrated may be used. Some components may be unnecessary. Also, the blocks are presented to illustrate some functional components. One or more of these blocks may be combined, divided, or combined and divided into different blocks when implemented in an illustrative embodiment.

For example, although inspection environment 200 includes composite structure 202, in some illustrative examples, inspection environment 200 may instead include a structure of any desirable material. For example, inspection environment 200 may include a structure made from any desirable material with a plurality of layers.

Figure 3:
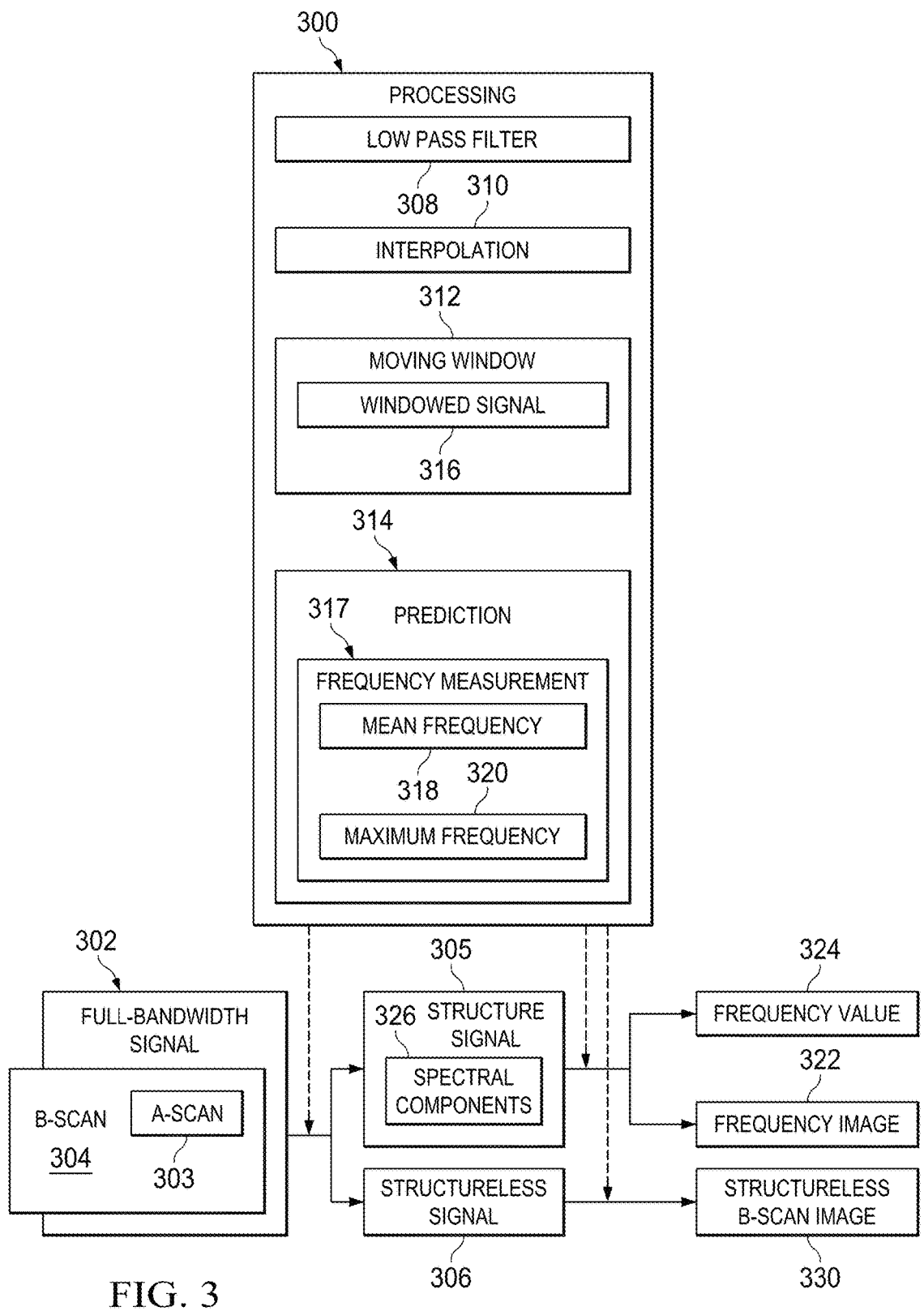
FIG. 3 is an illustration of a block diagram of processing of detector data in accordance with an illustrative embodiment.

Turning now to FIG. 3, an illustration of a block diagram of processing of detector data is depicted in accordance with an illustrative embodiment. Processing 300 of full-bandwidth signal 302 may be performed in computer system 214 of FIG. 2. Full-band width signal 302 may be the data collected by detector 208. The detector used may limit the bandwidth in full-bandwidth signal 302. In one illustrative example, the detector bandwidth maximum may be 10 MHz. A detector may be selected such that an expected structure signal is positioned within full-bandwidth signal 302. For example, if an expected structure signal is approximately 7 MHz, the detection bandwidth should be higher than 7 MHz. Processing 300 of full-bandwidth signal 302 may be performed by processor 215 of FIG. 2.

Full-bandwidth signal 302 may be all or part of data 240 of FIG. 2. In some illustrative examples, full-bandwidth signal 302 may be referred to as A-scan 303. A-scan 303 is a portion of B-scan 304. B-scan 304 may include further A-scans other than A-scan 303. A-scan 303 is data for a first location on a composite structure. The further A-scans of B-scan 304 include other locations of the same composite structure.

Full-bandwidth signal 302 undergoes processing 300 to create one of structure signal 305 or structureless signal 306. Structure signal 305 may be used to determine whether material changes, such as material changes 246 of FIG. 2 are present in a structure with a plurality of regular layers. In some illustrative examples, structure signal 305 is referred to as a regular structure signal. Structureless signal 306 increases detection of macroscopic inconsistencies in a structure with a plurality of layers. Structureless signal 306 depicts a clearer image of inconsistencies. In some illustrative examples, structureless signal 306 is referred to as a structureless ultrasonic A-scan.

Processing 300 includes any desirable series of operations. For example, processing 300 includes at least one of low-pass filter 308, interpolation 310, moving window 312, or prediction 314. The desirable series of operations of processing 300 are performed in any desirable order.

In one illustrative example, processing 300 on full-bandwidth signal 302 to form structure signal 305 includes moving window 312 and then prediction 314. In some illustrative examples, moving window 312 is a filter. In some illustrative examples, moving window 312 is applied to A-scan 303 in a time domain.

Moving window 312 is applied to full-bandwidth signal 302 such that only a few signals of full-bandwidth signal 302 are contained within moving window 312 during a period of time. In some illustrative examples, moving window 312 is a Gaussian shape. The Gaussian shape provides an advantageous tradeoff between frequency resolution and time resolution. Frequency resolution provides for precise removal and interpolation in the frequency domain. Time resolution provides for spatial resolution in a frequency image.

Moving window 312 is described in terms of sampling size or time. A minimum window size for moving window 312 is the duration of the interrogating pulse. Moving window 312 is typically larger than this duration to get better spectral resolution in the frequency domain. Duration in time domain is inversely proportional to resolution in frequency domain. The choice of characteristics for moving window 312 is determined by a tradeoff between required resolution in the frequency domain and required resolution in the time domain. As discussed above, a Gaussian shape may optimize this tradeoff.

Moving window 312 is sized such that moving window 312 only contains a desired number of plies. In one example, moving window 312 contains any desirable number of plies from two to seven plies. For example, moving window 312 may contain three plies. In another example, moving window 312 contains five plies.

In one illustrative example, moving window 312 has a diameter of 35 sample points (1/e level, 5 ns per sample), while time of flight within one ply of the composite structure is about 14 sample points. Thus, in this example, a windowed signal contains a few plies.

Each time moving window 312 is applied to full-bandwidth signal 302, windowed signal 316 is formed. For each windowed signal, prediction 314 may be performed. Prediction 314 determines frequency measurement 317. In one illustrative example, frequency measurement 317 is mean frequency 318. In another illustrative example, frequency measurement 317 is maximum frequency 320.

Mean frequency 318 may be determined using any desirable method. In one example, mean frequency 318 is determined using the autocorrelation function of the complex, analytic representation of windowed signal 316 of A-Scan 303, $\hat{R}(t)$, according to the following equation:

$$f_{mean} = \frac{1}{2\pi i} \frac{\dot{R}(0)}{R(0)} = \frac{1}{2\pi} \dot{\phi}(0) \tag{1}$$

R(0)—is the magnitude of the complex autocorrelation function, $\hat{R}(t)$, at time zero and $\emptyset(0)$ is the phase of the complex autocorrelation function at time zero. The dot above a function represents the time derivative of that function. For an N-point sampled version of the A-Scan, Eq. 1 becomes:

$$f_{mean} = \tan^{-1}\left[\frac{im R_N(1)}{re R_N(1)}\right] \tag{2}$$

where $R_N(1)$ is the N-point complex autocorrelation function $R_N$ evaluated at sample point 1, im refers to the imaginary part of the complex autocorrelation function and re refers to the real part of the complex autocorrelation function.

Mean frequency 318 is determined for each windowed signal 316 of full-bandwidth signal 302. Further, in some examples, mean frequency 318 is determined for other full-bandwidth signals other than full-bandwidth signal 302. For example, mean frequency 318 may be determined for each windowed signal 316 of each A-scan of B-scan 304.

In some illustrative examples, after determining mean frequency 318 of each windowed signal 316 of each A-scan of B-scan 304, the mean frequency 318 values are to form frequency image 322. Frequency image 322 may be an implementation of frequency image 268 of FIG. 2. Frequency image 322 includes each mean frequency 318 of each windowed signal 316 of each A-scan of B-scan 304. Material changes may be evident in frequency image 322. For example, intensity of the pixels of frequency image 322 indicates material changes.

In some illustrative examples, after determining mean frequency 318 of each windowed signal 316 of each A-scan of B-scan 304, the mean frequency 318 values are used to determine frequency value 324. Frequency value 324 may be indicative of material changes.

When frequency measurement 317 is maximum frequency 320, maximum frequency 320 may be predicted using any desirable method. In one example, maximum frequency 320 is predicted using the following equation:

$$S_n = \sum_{k=1}^{p} a_k * S_{n-k} \quad (3)$$

where p is a quantity of coefficients and $S_n$ is the A-scan signal at sample point n.

In another illustrative example, processing 300 on full-bandwidth signal 302 creates structureless signal 306. For example, moving window 312 is applied to full-bandwidth signal 302 in the time domain to form windowed signal 316. Prediction 314 may be performed for each windowed signal 316. In some illustrative examples, prediction 314 determines spectral components 326 of structure signal 305 using at least one of mean frequency 318 or maximum frequency 320. Spectral components 326 of structure signal 305 include a frequency and a width in the frequency domain.

Structure signal 305 is a component or part of the A-Scan in the time domain that results from the periodicity of the composite structure. Spectral components 326 are a component or part of the A-scan spectrum in the frequency domain that result from the periodicity of the composite structure. A corresponding function to a signal in the time domain is called the spectrum of the signal in the frequency domain, or the spectrum for short.

A Fourier transform of a signal results in a spectrum. An inverse Fourier transform of a spectrum results in a signal.

After determining spectral components 326 of structure signal 305, spectral components 326 of structure signal 305 may be removed from full-bandwidth signal 302. In one example, spectral components 326 of structure signal 305 are removed from an A-scan spectrum in the frequency domain. A region of the spectrum is left empty by removing spectral components 326 of structure signal 305 from full-bandwidth signal 302.

Interpolation 310 is performed to fill in the region of the spectrum left empty by removing spectral components 326 of structure signal 305 from full-bandwidth signal 302. Interpolation 310 is a method of constructing new data points between two points. Interpolation 310 may be performed using any desirable equation and by using any desirable mathematical method. Interpolation may be performed in the frequency domain. In one example, interpolation is performed on an A-scan spectrum. Interpolation 310 may take the form of linear interpolation. For examples, an inverse Fourier transformation is performed on the interpolated data to form A-scans in the time domain.

By performing interpolation 310, structureless signal 306 is formed. After completing interpolation 310, low-pass filter 308 may be used on structureless signal 306. Any desirable filter is used on structureless signal 306. In some illustrative examples, the filter may be represented by:

$$\text{Filter}(f) = \left(1 - \exp\left(-\left(\frac{f}{f_0}\right)^2\right)\right) * \exp\left(-\left(\frac{f}{f_1}\right)^2 - \left(\frac{f}{f_2}\right)^4\right) \quad (4)$$

In one illustrative example, the parameters may include: $f_0 = 100$ kHz, $f_1 = 11$ MHz, and $$\frac{f_2}{f_1} = 1.2$$

In some illustrative examples, instead of 11 MHz, $f_1 = 5$ MHz. In this case microscopic inhomogeneities with a size smaller than the regular structure period will be also removed from the band-pass filtered signal. Thus large-scale inconsistencies will be emphasized.

After using low-pass filter 308, the filtered and interpolated data in the time domain may be used to display structureless B-scan image 330. Structureless B-scan image 330 indicates both macroscopic inconsistencies, such as porosity, delamination, or other macroscopic inconsistencies, or microscopic inconsistencies. Microscopic inconsistencies may be inconsistencies of a size smaller than the period of regular structure.

Turning now to FIG. 4, an illustration of an ultrasonic A-scan spectrum in the frequency domain is depicted in accordance with an illustrative embodiment. Image 400 may be a physical implementation of image 253 of FIG. 2. Image 400 includes A-scan spectrum 402. A-scan spectrum 402 in the frequency domain is computed from the Fourier Transform of the A-Scan. A-scan spectrum 402 is an example of ultrasonic A-scan spectrum 259 in frequency domain 264 of FIG. 2. A-scan spectrum 402 is a Fourier Transform of ultrasonic A-scan 258 in time domain 266.

A-scan spectrum 402 includes spectral components 404 of a structure signal (not depicted). Spectral components 404 may be identified using a prediction. Image 400 has x-axis 406 and y-axis 408. In this example, A-scan spectrum 402 is in frequency domain. Accordingly, x-axis 406 is frequency in MHz and y-axis 408 is magnitude. Spectral region 410 around spectral components 404 can be defined based on the width of the structure signal spectrum. In this illustrative embodiment, spectral region 410 is the mean frequency±two times the width of the spectrum associated with spectral components 404. The width of the structural signal spectrum in the frequency domain is estimated using an autocorrelation function of a complex, analytic representation of the windowed signal of an ultrasonic A-Scan, $\hat{R}(t)$. For an N-point sampled version of the A-Scan, $$\text{width} = \frac{2}{N}\left[1 - \frac{|R_N(1)|}{R_N(0)}\right],$$

where $|R_N(1)|$ is the magnitude of the N-point complex autocorrelation function $R_N$ evaluated at sample point 1 and $R_N(0)$ is the N-point complex autocorrelation function $R_N$ evaluated at sample point 0.

Turning now to FIG. 5, an illustration of an interpolated ultrasonic A-scan spectrum in the frequency domain is depicted in accordance with an illustrative embodiment. Image 500 is a physical implementation of image 253 of FIG. 2. Image 500 includes A-scan spectrum 502. A-scan spectrum 502 in the frequency domain is computed from the Fourier Transform of the A-Scan. A-scan spectrum 502 is an example of ultrasonic A-scan spectrum 259 in frequency domain 264 of FIG. 2. A-scan spectrum 402 is a Fourier transform of ultrasonic A-scan 258 in frequency domain 264 of FIG. 2.

A-scan spectrum 502 in the frequency domain is a view of A-scan spectrum 402 in the frequency domain with spectral components 404 of the structure signal removed. Image 500 has x-axis 504 and y-axis 506. X-axis 504 is frequency in MHz. Y-axis 506 is magnitude.

As can be seen from image 500, A-scan spectrum 502 includes region 508. Region 508 includes a number of points created by interpolation. In this illustrative example, interpolation takes the form of linear interpolation. Region 508 has the same width as spectral region 410 of FIG. 4. Region 508 is a portion of A-scan spectrum 502 from which spectral components 404 were removed.

A-Scan spectrum 502 in FIG. 5 is presented in the frequency domain. The equivalent time domain representation as an A-Scan can be obtained by inverse Fourier transforming A-Scan spectrum 502 in image 500.

Figure 6:
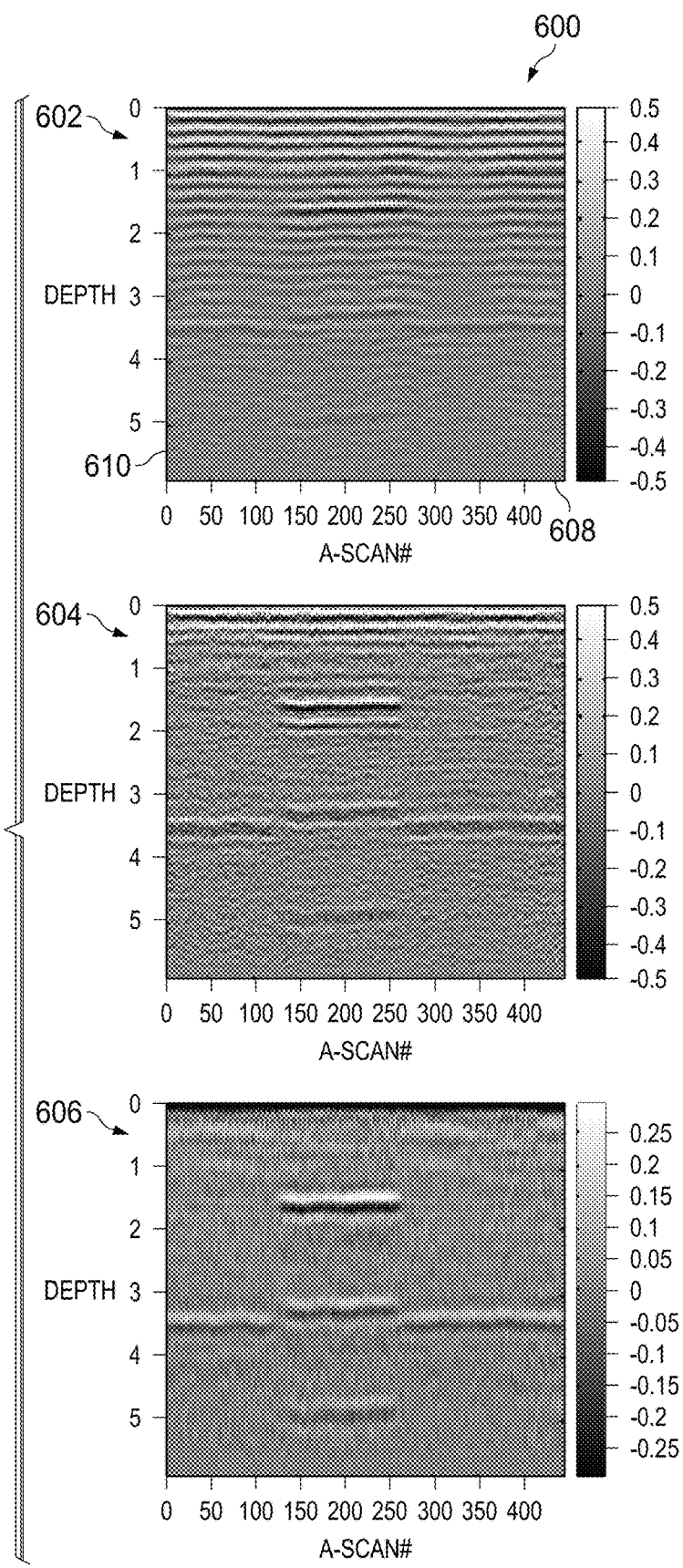
FIG. 6 is an illustration of three B-scans in accordance with an illustrative embodiment.

Turning now to FIG. 6, an illustration of three B-scans is depicted in accordance with an illustrative embodiment. Image 600 is a physical implementation of image 253 of FIG. 2. Image 600 includes B-scan 602, B-scan 604, and B-scan 606. B-scan 602, B-scan 604, and B-scan 606 are each examples of B-scan 260 in FIG. 2. Each of B-scan 602, B-scan 604, and B-scan 606 are formed from data in the time domain.

B-scan 602 is a B-scan image of a full-bandwidth signal without structure removal processing. B-scan 602 is formed from A-scans in the time domain with no processing.

B-scan 604 is a B-scan image of a full-bandwidth signal with spectral components of a structure signal removed and interpolation in the frequency domain. For example, B-scan 604 is an image of B-scan 602 without the structure signal. Spectral components of a structure signal are identified by processing an A-scan in the time domain. An A-scan spectrum in the frequency domain is created by performing a Fourier transform on the A-scan. Afterwards, the spectral components identified are removed from the A-scan spectrum in the frequency domain. The interpolation may also occur in the A-scan spectrum in the frequency domain. Afterwards, an inverse Fourier transform is performed to transform the A-scan spectrum without the spectral components of the structure signal into the time domain and form an A-scan.

B-scan 606 is a low-pass filtered B-scan image following removal of the spectral components of the structure signal and interpolation in the frequency domain. For example, B-scan 606 is an image of B-scan 604 after a low-pass filter is applied.

As can be seen in image 600, inconsistencies in B-scan 606 are more defined than inconsistencies in either B-scan 604 or B-scan 602. Thus, removing spectral components of a structure signal from a full-bandwidth signal improves detectability of inconsistencies. B-scan 602 has x-axis 608 and y-axis 610. X-axis 608 is scanning distance expressed as A-scan number. Y-axis 610 is depth.

By removing spectral components of the structure signal, the low-pass filter has been extended compared to direct filtering of the full bandwidth signal. A higher bandwidth low-pass filter provides higher spatial resolution in the B-scan 606 depicted inconsistencies.

Figure 7:
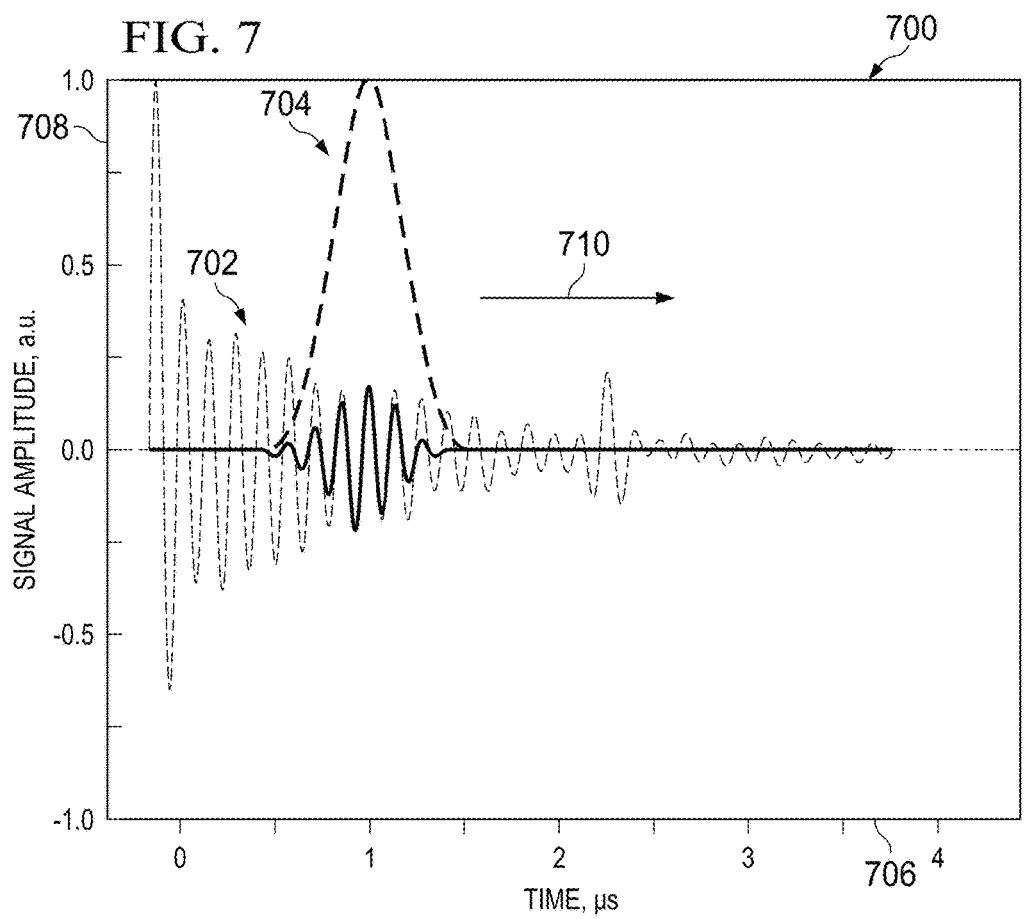
FIG. 7 is an illustration of a moving window on an ultrasonic A-scan in the time domain in accordance with an illustrative embodiment.

Turning now to FIG. 7, an illustration of a moving window on an ultrasonic A-scan in the time domain is depicted in accordance with an illustrative embodiment. Image 700 is a physical implementation of image 253 of FIG. 2. Image 700 includes A-scan 702. A-scan 702 is an example of ultrasonic A-scan 258 in time domain 266 of FIG. 2. Moving window 704 is positioned over A-scan 702.

Image 700 has x-axis 706 and y-axis 708. In this example, A-scan 702 is in the time domain. Accordingly, x-axis 706 is time in microseconds and y-axis 708 is amplitude.

Moving window 704 is applied to A-scan 702 to determine frequency measurements. Moving window 704 includes a number of plies of the composite structures. In this illustrative example, moving window 704 includes five plies for A-scan 702.

Moving window 704 is moved in direction 710 in image 700 to form a number of windowed signals. Frequency measurements may be determined for each windowed signal of A-scan 702. The frequency measurements of A-scan 702 are used to determine whether material changes have occurred in the composite structure of A-scan 702. In one example, the frequency measurements of A-scan 702 are used to form a frequency image.

In some illustrative examples, frequency measurements of A-scan 702 are used to increase the detectability of inconsistencies. For example, frequency measurements of A-scan 702 are used to predict spectral components of the structure signal. The spectral components of the structure signal are then removed from the full-bandwidth signal and an interpolation in the frequency domain performed. In some illustrative examples, the interpolation and the removal of the spectral components of the structure signal are performed simultaneously. For example, the interpolation removes the spectral components of the structure signal. In other illustrative examples, the structure signal is removed prior to interpolating. The interpolated signal is then be used to form a B-scan.

Figure 8:
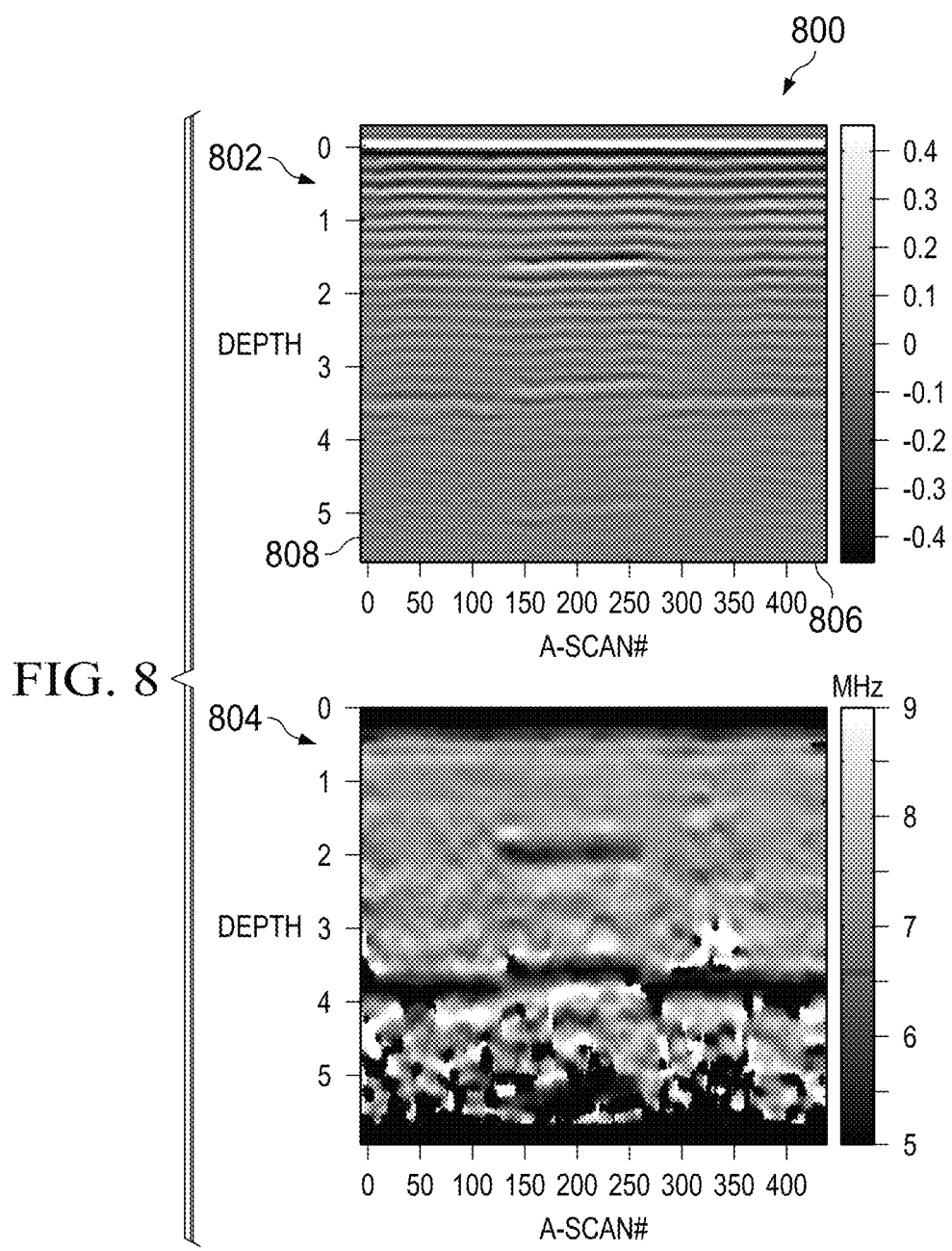
FIG. 8 is an illustration of a B-scan image and a frequency image in accordance with an illustrative embodiment.

Turning now to FIG. 8, an illustration of a B-scan image and a frequency image is depicted in accordance with an illustrative embodiment. Image 800 is a physical implementation of image 253 of FIG. 2. Image 800 includes B-scan image 802 and frequency image 804. Frequency image 804 is an example of frequency image 268 in FIG. 2. B-scan image 802 and frequency image 804 has x-axis 806 and y-axis 808. As depicted, x-axis 806 is distance as described in an A-scan number. Y-axis 808 is depth.

Frequency image 804 is an image of frequency measurements for the composite structure. As can be seen in image 800, inconsistencies in frequency image 804 have increased detectability.

The different components shown in FIG. 1 and FIGS. 3-8 may be combined with components in FIG. 2, used with components in FIG. 2, or a combination of the two. Additionally, some of the components in FIG. 1 and FIGS. 3-8 may be illustrative examples of how components shown in block form in FIG. 2 may be implemented as physical structures.

Figure 9:
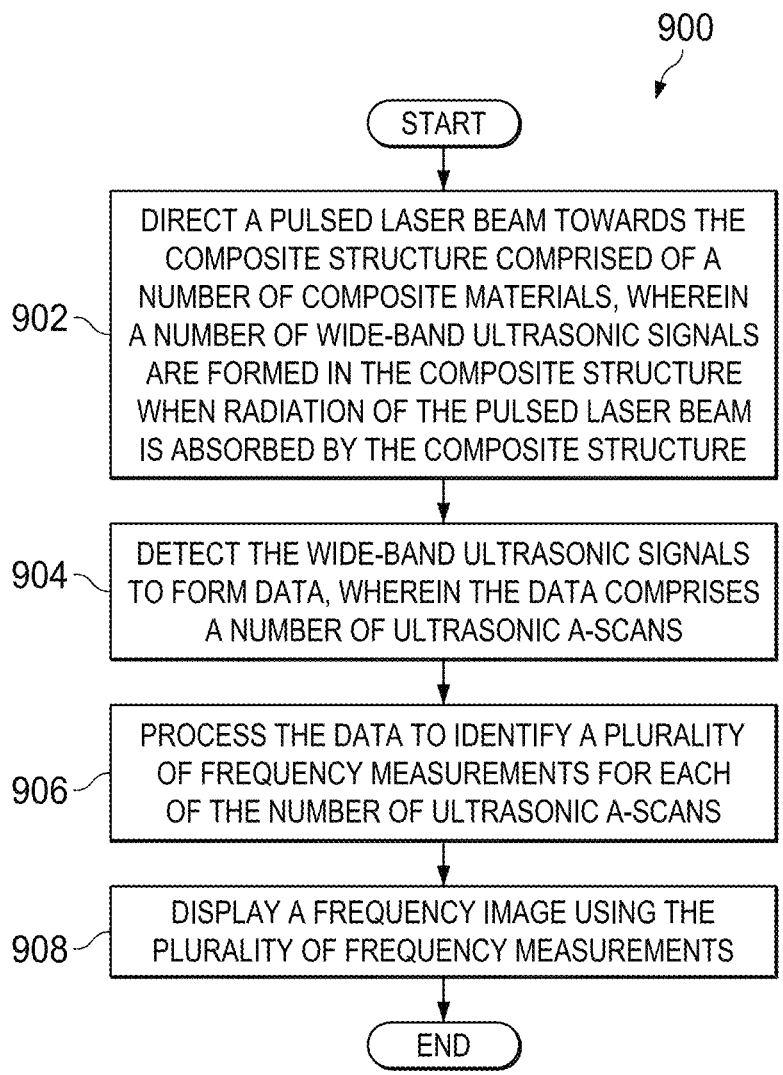
FIG. 9 is an illustration of a flowchart of a process for detecting material changes in a composite structure in accordance with an illustrative embodiment.

Turning now to FIG. 9, an illustration of a flowchart of a process for detecting material changes in a composite structure is depicted in accordance with an illustrative embodiment. The process illustrated in FIG. 9 may be implemented in an ultrasound inspection system such as laser ultrasound inspection system 205 in FIG. 2.

Process 900 begins by directing a pulsed laser beam towards the composite structure comprised of a number of composite materials, wherein wide-band ultrasonic signals are formed in the composite structure when radiation of the pulsed laser beam is absorbed by the composite structure (operation 902). Process 900 then detects the wide-band ultrasonic signals to form data, wherein the data comprises a number of ultrasonic A-scans (operation 904). In some illustrative examples, the wide-band ultrasonic signals are detected using a point-like optical detector. In some examples, the point-like optical detector of ultrasound is broadband.

Process 900 also processes the data to identify a plurality of frequency measurements for each of the number of ultrasonic A-scans (operation 906). In some examples, the frequency measurements are selected from at least one of mean frequencies or maximum frequencies. In some illustrative examples, processing the data comprises applying a moving window to each of the number of ultrasonic A-scans and determining at least one of a mean frequency or a maximum frequency within the moving window. In some illustrative examples, the moving window has a Gaussian shape.

In one illustrative example, processing the data comprises determining a maximum frequency of a windowed signal of an A-scan of the number of ultrasonic A-scans according to the following equation:

$$S_n = \Sigma_{k=1}^{P} a_k * S_{n-k} \tag{5}$$

In this equation, p is a quantity of coefficients and $S_n$ is the A-scan signal at sample point n.

In another illustrative example, processing the data to identify the frequency measurements comprises determining a mean frequency of a windowed signal of an ultrasonic A-scan of the number of ultrasonic A-scans using the autocorrelation function of the complex, analytic representation of the windowed signal of the ultrasonic A-Scan, $\hat{R}(t)$, according to the following equation:

$$f_{mean} = \frac{1}{2\pi i} \frac{\dot{R}(0)}{R(0)} = \frac{1}{2\pi} \dot{\phi}(0) \tag{6}$$

where $R(0)$ is the magnitude of the complex autocorrelation function, $\hat{R}(t)$, at time zero, and $\emptyset(0)$ is the phase of the complex autocorrelation function at time zero. The dot above a function represents the time derivative of that function. For an N-point sampled version of the A-Scan, Eq. 5 becomes:

$$f_{mean} = \tan^{-1}\left[\frac{im R_N(1)}{re R_N(1)}\right] \tag{7}$$

where $R_N(1)$ is the N-point complex autocorrelation function $R_N$ evaluated at sample point 1, im refers to the imaginary part of the complex autocorrelation function and re refers to the real part of the complex autocorrelation function.

Process 900 further displays a frequency image using the plurality of frequency measurements (operation 908). Afterwards, the process terminates.

By analyzing the frequency image, inconsistencies may be observed. For example, by analyzing the frequency image, material changes may be observed. In some illustrative examples, if material changes are observed, the composite structure may be reworked or replaced.

Figure 10:
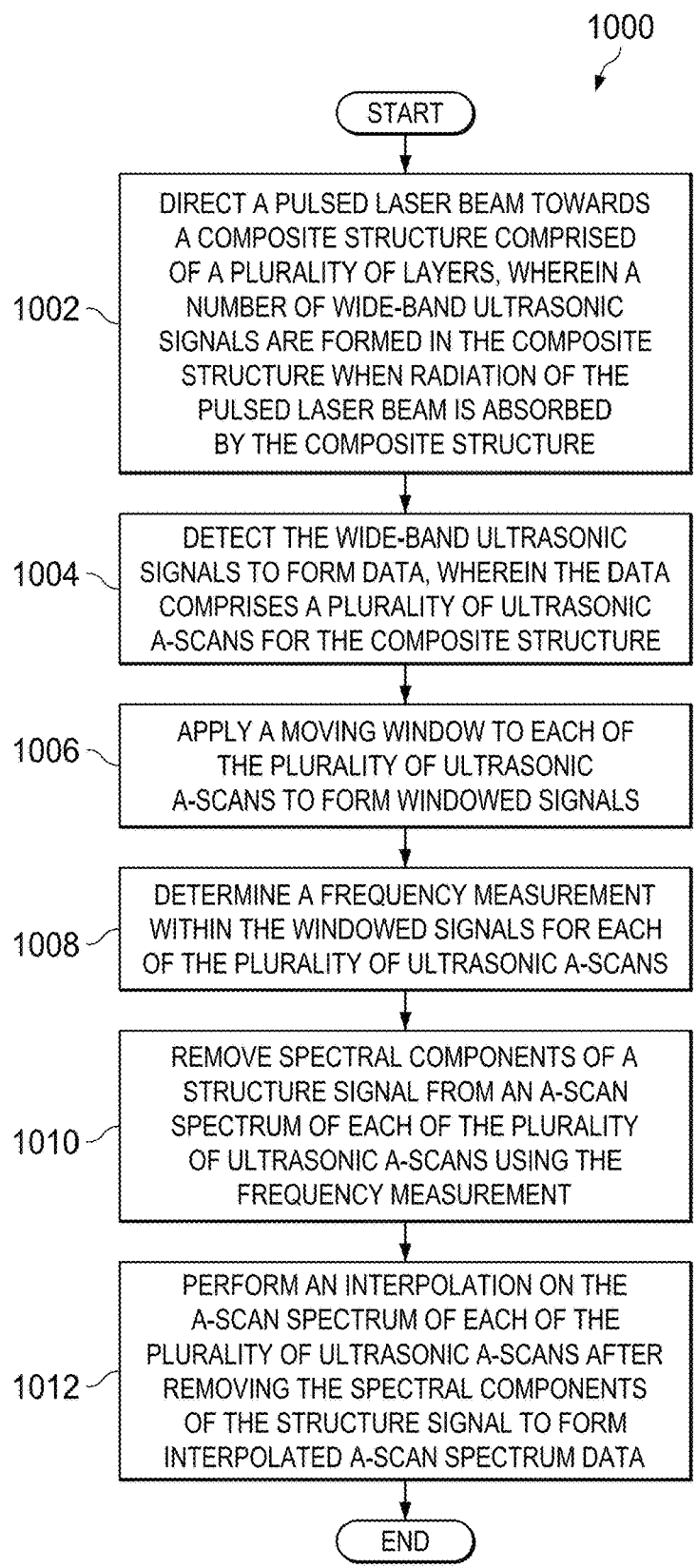
FIG. 10 is an illustration of a flowchart of a process for processing data to improve detection of inconsistencies in accordance with an illustrative embodiment.

Turning now to FIG. 10, an illustration of a flowchart of a process for processing data to improve detection of inconsistencies is depicted in accordance with an illustrative embodiment. The process illustrated in FIG. 10 may be implemented in an ultrasound inspection system such as laser ultrasound inspection system 205 in FIG. 2.

Process 1000 begins by directing a pulsed laser beam towards a composite structure comprised of a plurality of layers, wherein a number of wide-band ultrasonic signals are formed in the composite structure when radiation of the pulsed laser beam is absorbed by the composite structure (operation 1002). Process 1000 also detects the wide-band ultrasonic signals to form data, wherein the data comprises a plurality of ultrasonic A-scans for the composite structure (operation 1004).

Process 1000 applies a moving window to each of the plurality of A-scans to form windowed signals (operation 1006). Process 1000 determines a frequency measurement within the windowed signals for each of the plurality of ultrasonic A-scans (operation 1008). In some illustrative examples, the frequency measurement is selected from a mean frequency or a maximum frequency.

In some illustrative examples, the maximum frequency is determined according to the following equation:

$$S_n = \Sigma_{k=1}^{P} a_k * S_{n-k} \tag{8}$$

In this equation, p is a quantity of coefficients and $S_n$ is the A-scan signal at sample point n.

In some illustrative examples, the mean frequency is determined using the autocorrelation function of the complex, analytic representation of the windowed signal of the A-can, $\hat{R}(t)$, according to the equation:

$$f_{mean} = \frac{1}{2\pi i} \frac{\dot{R}(0)}{R(0)} = \frac{1}{2\pi} \dot{\phi}(0) \tag{9}$$

where $R(0)$ is the magnitude of the complex autocorrelation function, $\hat{R}(t)$, at time zero and $\emptyset(0)$ is the phase of the complex autocorrelation function at time zero, and the dot above a function represents the time derivative of that function. For an N-point sampled version of the A-Scan, Eq. 7 becomes:

$$f_{mean} = \tan^{-1}\left[\frac{im R_N(1)}{re R_N(1)}\right] \tag{10}$$

where $R_N(1)$ is the N-point complex autocorrelation function $R_N$ evaluated at sample point 1, im refers to the imaginary part of the complex autocorrelation function and re refers to the real part of the complex autocorrelation function.

Process 1000 also removes spectral components of a structure signal from an A-scan spectrum of each of the plurality of ultrasonic A-scans using the frequency measurement (operation 1010). Process 1000 performs an interpolation on the A-scan spectrum of each of the plurality of ultrasonic A-scans after removing the spectral components of the structure signal to form interpolated A-scan spectrum data (operation 1012). Afterwards, the process terminates.

Figure 11:
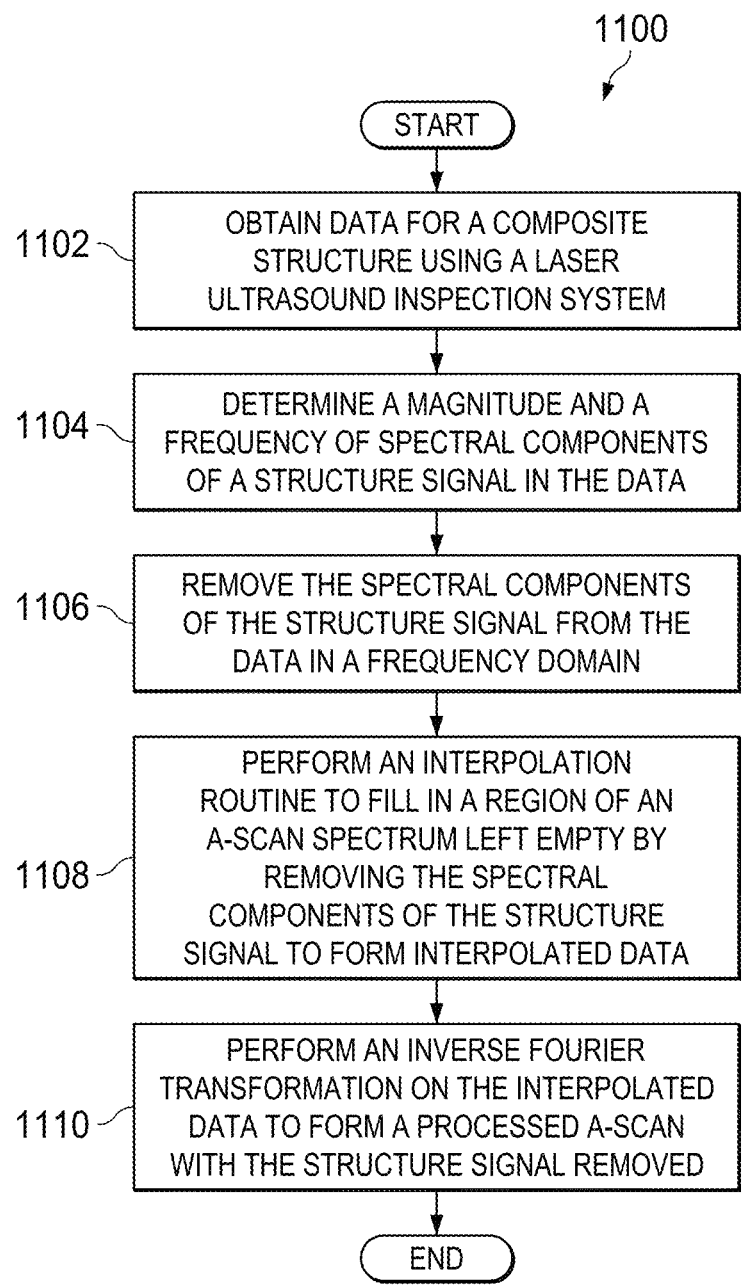
FIG. 11 is an illustration of a flowchart of a process for processing data to improve detection of inconsistencies in accordance with an illustrative embodiment.

Turning now to FIG. 11, an illustration of a flowchart of a process for processing data to improve detection of inconsistencies in accordance with an illustrative embodiment. The process illustrated in FIG. 11 may be implemented in an ultrasound inspection system such as laser ultrasound inspection system 205 in FIG. 2.

Process 1100 begins by obtaining data for a composite structure using a laser ultrasound inspection system (operation 1102). In some illustrative examples, the composite structure has a plurality of layers.

Process 1100 determines a width and a frequency of spectral components of a structure signal in the data (operation 1104). In some illustrative examples, the frequency of the spectral components of the structure signal is estimated using the following equation:

$$S_n = \Sigma_{k=1}^{p} a_k * S_{n-k} \quad (11)$$

where p is a quantity of coefficients and $S_n$ is the A-scan signal at sample point n.

In some illustrative examples, the frequency of the spectral components of the structure signal is estimated using the autocorrelation function of the complex, analytic representation of the windowed signal of the ultrasonic A-Scan, $\hat{R}(t)$, according to the following equation:

$$f_{mean} = \frac{1}{2\pi i} \frac{\dot{R}(0)}{R(0)} = \frac{1}{2\pi} \dot{\phi}(0) \quad (12)$$

where R(0) is the magnitude of the complex autocorrelation function, $\hat{R}(t)$, at time zero, and $\emptyset(0)$ is the phase of the complex autocorrelation function at time zero. The dot above a function represents the time derivative of that function. For an N-point sampled version of the A-Scan, Eq. 9 becomes:

$$f_{mean} = \tan^{-1}\left[\frac{\mathrm{im}R_N(1)}{\mathrm{re}R_N(1)}\right] \quad (13)$$

where $R_N(1)$ is the N-point complex autocorrelation function $R_N$ evaluated at sample point 1, im refers to the imaginary part of the complex autocorrelation function and re refers to the real part of the complex autocorrelation function.

In some illustrative examples, the width of the structural signal spectrum in the frequency domain is estimated using an autocorrelation function of a complex, analytic representation of the windowed signal of an ultrasonic A-Scan, $\hat{R}(t)$. For an N-point sampled version of the A-Scan, $$\mathrm{width} = \frac{2}{N}\left[1 - \frac{|R_N(1)|}{R_N(0)}\right],$$

where $|R_N(1)|$ is the magnitude of the N-point complex autocorrelation function $R_N$ evaluated at sample point 1 and $R_N(0)$ is the N-point complex autocorrelation function $R_N$ evaluated at sample point 0.

Process 1100 removes the spectral components of the structure signal from the data in the frequency domain (operation 1108). Process 1100 performs an interpolation routine to fill in a region of an A-scan spectrum left empty by removing the spectral components of the structure signal to form interpolated data (operation 1106). Process 1100 performs an inverse Fourier transformation on the interpolated data to form a processed A-scan with the structure signal removed (operation 1108). In some illustrative example, the processed A-scan with the structure signal removed may also be referred to as a structureless signal, such as structureless signal 306 of FIG. 3. Afterwards the process terminates.

The flowcharts and block diagrams in the different depicted embodiments illustrate the architecture, functionality, and operation of some possible implementations of apparatus and methods in an illustrative embodiment. In this regard, each block in the flowcharts or block diagrams may represent a module, a segment, a function, and/or a portion of an operation or step.

In some alternative implementations of an illustrative embodiment, the function or functions noted in the blocks may occur out of the order noted in the figures. For example, in some cases, two blocks shown in succession may be executed substantially concurrently, or the blocks may sometimes be performed in the reverse order, depending upon the functionality involved. Also, other blocks may be added in addition to the illustrated blocks in a flowchart or block diagram.

For example, process 900 may further comprise determining whether undesirable conditions are present in the composite structure by analyzing the frequency image. In some illustrative examples, the undesirable conditions include material changes.

In a further example, process 1000 further comprises Fourier transforming each of the plurality of ultrasonic A-scans to form the A-scan spectrum of each of the plurality of ultrasonic A-scans; and performing an inverse Fourier transformation on the interpolated A-scan spectrum data to form a plurality of structureless ultrasonic A-scans. Process 1000 may further comprise filtering a structureless B-scan image formed from the plurality of structureless ultrasonic A-scans. In one example, filtering the structureless B-scan image comprises using a low-pass filter on the structureless B-scan image.

In another example, process 1100 further comprises filtering the A-scan to form filtered data. Process 1100 may also comprise displaying the filtered data in a B-scan.

Figure 12:
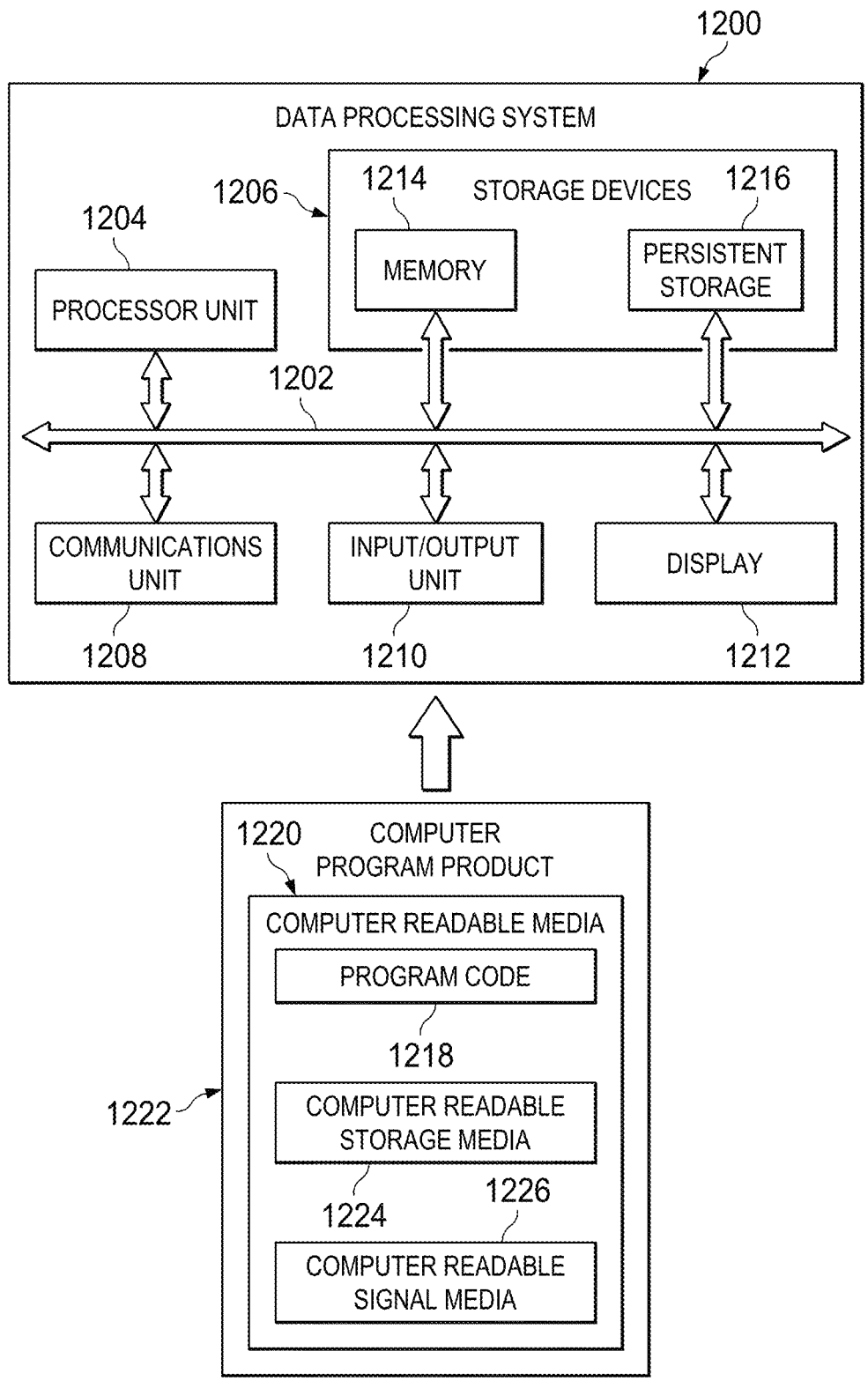
FIG. 12 is an illustration of a data processing system in the form of a block diagram in accordance with an illustrative embodiment.

Turning now to FIG. 12, an illustration of a data processing system in the form of a block diagram is depicted in accordance with an illustrative embodiment. Data processing system 1200 may be used to implement computer system 214 of FIG. 2. Data processing system 1200 may be used to process data as described in FIG. 3 and display output as depicted in FIGS. 4-8. As depicted, data processing system 1200 includes communications framework 1202, which provides communications between processor unit 1204, storage devices 1206, communications unit 1208, input/output unit 1210, and display 1212. In some cases, communications framework 1202 may be implemented as a bus system.

Processor unit 1204 is configured to execute instructions for software to perform a number of operations. Processor unit 1204 may comprise a number of processors, a multi-processor core, and/or some other type of processor, depending on the implementation. In some cases, processor unit 1204 may take the form of a hardware unit, such as a circuit system, an application specific integrated circuit (ASIC), a programmable logic device, or some other suitable type of hardware unit.

Instructions for the operating system, applications, and/or programs run by processor unit 1204 may be located in storage devices 1206. Storage devices 1206 may be in communication with processor unit 1204 through communications framework 1202. As used herein, a storage device, also referred to as a computer readable storage device, is any piece of hardware capable of storing information on a temporary and/or permanent basis. This information may include, but is not limited to, data, program code, and/or other information.

Memory 1214 and persistent storage 1216 are examples of storage devices 1206. Memory 1214 may take the form of, for example, a random access memory or some type of volatile or non-volatile storage device. Persistent storage 1216 may comprise any number of components or devices. For example, persistent storage 1216 may comprise a hard drive, a flash memory, a rewritable optical disk, a rewritable magnetic tape, or some combination of the above. The media used by persistent storage 1216 may or may not be removable.

Communications unit 1208 allows data processing system 1200 to communicate with other data processing systems and/or devices. Communications unit 1208 may provide communications using physical and/or wireless communications links.

Input/output unit 1210 allows input to be received from and output to be sent to other devices connected to data processing system 1200. For example, input/output unit 1210 may allow user input to be received through a keyboard, a mouse, and/or some other type of input device. As another example, input/output unit 1210 may allow output to be sent to a printer connected to data processing system 1200.

Display 1212 is configured to display information to a user. Display 1212 may comprise, for example, without limitation, a monitor, a touch screen, a laser display, a holographic display, a virtual display device, and/or some other type of display device.

In this illustrative example, the processes of the different illustrative embodiments may be performed by processor unit 1204 using computer-implemented instructions. These instructions may be referred to as program code, computer usable program code, or computer readable program code, and may be read and executed by one or more processors in processor unit 1204.

In these examples, program code 1218 is located in a functional form on computer readable media 1220, which is selectively removable, and may be loaded onto or transferred to data processing system 1200 for execution by processor unit 1204. Program code 1218 and computer readable media 1220 together form computer program product 1222. In this illustrative example, computer readable media 1220 may be computer readable storage media 1224 or computer readable signal media 1226.

Computer readable storage media 1224 is a physical or tangible storage device used to store program code 1218 rather than a medium that propagates or transmits program code 1218. Computer readable storage media 1224 may be, for example, without limitation, an optical or magnetic disk or a persistent storage device that is connected to data processing system 1200.

Alternatively, program code 1218 may be transferred to data processing system 1200 using computer readable signal media 1226. Computer readable signal media 1226 may be, for example, a propagated data signal containing program code 1218. This data signal may be an electromagnetic signal, an optical signal, and/or some other type of signal that can be transmitted over physical and/or wireless communications links.

The illustration of data processing system 1200 in FIG. 12 is not meant to provide architectural limitations to the manner in which the illustrative embodiments may be implemented. The different illustrative embodiments may be implemented in a data processing system that includes components in addition to or in place of those illustrated for data processing system 1200. Further, components shown in FIG. 12 may be varied from the illustrative examples shown.

Figure 13:
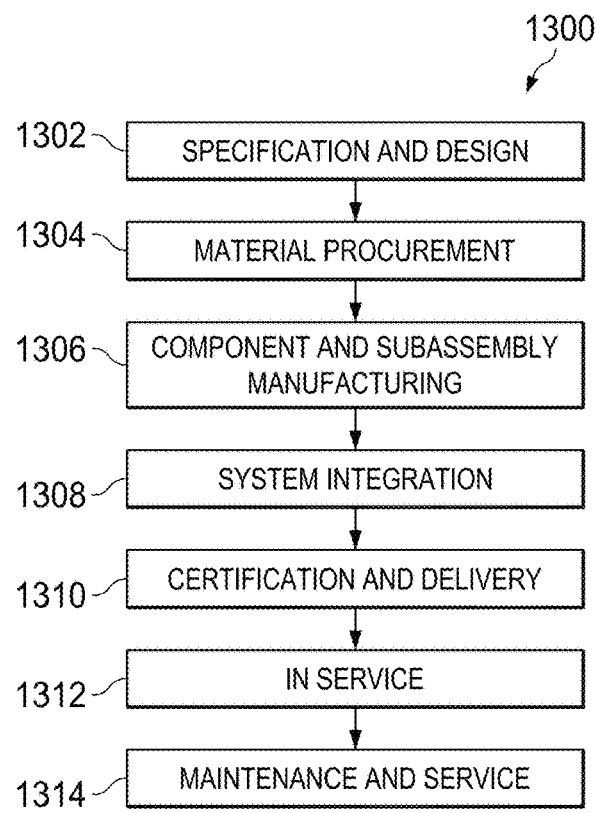
FIG. 13 is an illustration of an aircraft manufacturing and service method in the form of a block diagram in accordance with an illustrative embodiment.
Figure 14:
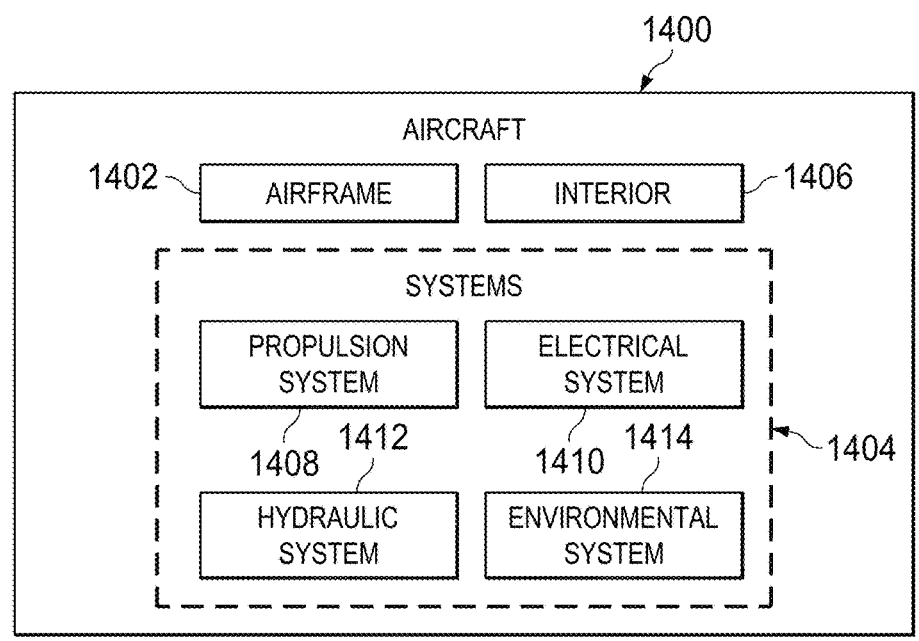
FIG. 14 is an illustration of an aircraft in the form of a block diagram in which an illustrative embodiment may be implemented.

Illustrative embodiments of the disclosure may be described in the context of aircraft manufacturing and service method 1300, as shown in FIG. 13, and aircraft 1400, as shown in FIG. 14. Turning first to FIG. 13, an illustration of an aircraft manufacturing and service method is depicted in accordance with an illustrative embodiment. During pre-production, aircraft manufacturing and service method 1300 may include specification and design 1302 of aircraft 1400 and material procurement 1304.

During production, component and subassembly manufacturing 1306 and system integration 1308 of aircraft 1400 takes place. Thereafter, aircraft 1400 may go through certification and delivery 1310 in order to be placed in service 1312. While in service 1312 by a customer, aircraft 1400 is scheduled for routine maintenance and service 1314, which may include modification, reconfiguration, refurbishment, and other maintenance or service.

Each of the processes of aircraft manufacturing and service method 1300 may be performed or carried out by a system integrator, a third party, and/or an operator. In these examples, the operator may be a customer. For the purposes of this description, a system integrator may include, without limitation, any number of aircraft manufacturers and major-system subcontractors; a third party may include, without limitation, any number of vendors, subcontractors, and suppliers; and an operator may be an airline, a leasing company, a military entity, a service organization, and so on.

With reference now to FIG. 14, an illustration of an aircraft is depicted in which an illustrative embodiment may be implemented. In this example, aircraft 1400 is produced by aircraft manufacturing and service method 1300 in FIG. 13, and may include airframe 1402 with plurality of systems 1404 and interior 1406. Examples of plurality of systems 1404 include one or more of propulsion system 1408, electrical system 1410, hydraulic system 1412, and environmental system 1414. Any number of other systems may be included. Although an aerospace example is shown, different illustrative embodiments may be applied to other industries, such as the automotive industry.

Apparatuses and methods embodied herein may be employed during at least one of the stages of aircraft manufacturing and service method 1300 in FIG. 13. One or more illustrative embodiments may be used during component and subassembly manufacturing 1306 in FIG. 13. For example, laser ultrasound inspection system 205 in FIG. 2 may be used to inspect composite structures during component and subassembly manufacturing 1306. Further, laser ultrasound inspection system 205 in FIG. 2 may be used to inspect an assembly during maintenance and service 1314 in FIG. 13. For example, composite structures of aircraft 1400 may be inspected during scheduled maintenance for aircraft 1400 using laser ultrasound inspection system 205.

Thus, one or more illustrative embodiments provide a method and apparatus for determining whether inconsistencies are present in a composite structure. A structure signal is identified. After identifying the structure signal, a B-scan is formed using the structure signal. The B-scan is analyzed to determine whether inconsistencies are present in the periodicity of the structure. In some illustrative examples, a structure signal is predicted by frequency measurements. In some examples, the frequency measurements are used to form a frequency image. The frequency image is analyzed to determine whether inconsistencies are present in the periodicity of the structure. For example, the inconsistencies in the periodicity of the structure may include material changes.

In another example, after identifying the structure signal, the spectral components of the structure signal are removed from the full-bandwidth signal spectrum. The region of the A-Scan spectrum left empty by removing the spectral components of the structural signal are filled by an interpolation. The signal including the interpolation, after inverse Fourier transform, is used to form a B-scan. The B-scan has increased detectability for inconsistencies.

By determining a structure signal, the illustrative embodiments detect inconsistencies that conventional processing would not detect. For example, the illustrative embodiments detect material changes. As another example, the illustrative embodiments detect inconsistencies previously masked by a structure signal.

In one illustrative example, a method of detecting material changes in a composite structure is presented. A pulsed laser beam is directed towards the composite structure comprised of a number of composite materials. Wide-band ultrasonic signals are formed in the composite structure when radiation of the pulsed laser beam is absorbed by the composite structure. The wide-band ultrasonic signals are detected to form data. The data comprises a number of ultrasonic A-scans. Ultrasonic A-scans consist of the information on both of a regular composite structure and inconsistencies. The regular composite structure is related with the designed packing of individual layers during manufacturing. The inconsistencies include at least one of voids, flaws, artificial inclusions, or other types of inconsistencies. A moving window in the time domain is applied to each of the plurality of ultrasonic A-scans to form windowed signals. A frequency measurement is determined within the windowed signals for each of the plurality of A-scans. The frequency measurement determined for each of the windowed signal form the plurality of characteristic frequencies describing the regular structure of composite. An image of characteristic frequencies is displayed using the plurality of frequency measurements. The changes in the regular structure of material are represented in the characteristic frequency image.

In another illustrative embodiment, a method is presented. A pulsed laser beam is directed towards a composite structure comprised of a plurality of layers. A number of wide-band ultrasonic signals are formed in the composite structure when radiation of the pulsed laser beam is absorbed by the composite structure. The wide-band ultrasonic signals are detected to form data. The data comprises a plurality of ultrasonic A-scans for the composite structure. A Fourier spectrum for the plurality of ultrasonic A-scans is calculated. A frequency peak, characterizing the regular material structure, of entire A-scan frequency spectrum is determined for the plurality of ultrasonic A-scans. Spectral components of a structure signal are removed from a full-bandwidth signal spectrum of each of the plurality of ultrasonic A-scans using an interpolation of the signal spectra around the frequency peak in the Fourier domain to form the interpolated data and performing the inverse Fourier transformation applied to the interpolated signal spectra.

The description of the different illustrative embodiments has been presented for purposes of illustration and description, and is not intended to be exhaustive or limited to the embodiments in the form disclosed. Many modifications and variations will be apparent to those of ordinary skill in the art. Further, different illustrative embodiments may provide different features as compared to other desirable embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. A method of detecting material changes in a composite structure, the method comprising:
    directing a pulsed laser beam towards the composite structure comprised of a number of composite materials, wherein wide-band ultrasonic signals are formed in the composite structure when radiation of the pulsed laser beam is absorbed by the composite structure;
    detecting the wide-band ultrasonic signals to form data, wherein the data comprises a number of ultrasonic A-scans;
    processing the data to identify a plurality of frequency measurements for each of the number of ultrasonic A-scans; and
    displaying a frequency image using the plurality of frequency measurements, wherein the material changes are represented in the frequency image, wherein a first axis of the frequency image is one of time or depth, and wherein an intensity of each pixel of the frequency image is indicative of a frequency measurement of the plurality of frequency measurements.

2. The method of claim 1, wherein processing the data comprises:
    applying a moving window to each of the number of ultrasonic A-scans, wherein the moving window is a filter; and
    determining at least one of a mean frequency or a maximum frequency within the moving window.

3. The method of claim 2, wherein the moving window has a Gaussian shape.

4. The method of claim 1 further comprising:
    determining whether undesirable conditions are present in the composite structure by analyzing the frequency image, wherein the undesirable conditions include the material changes.

5. The method of claim 1, wherein the plurality of frequency measurements are selected from at least one of mean frequencies or maximum frequencies.

6. The method of claim 1, wherein processing the data comprises:
    determining a maximum frequency of a windowed signal of an A-scan of the number of ultrasonic A-scans using the equation $S_n = \Sigma_{k=1}^{p} a_k * S_{n-k}$, where p is a quantity of coefficients and $S_n$ is an A-scan signal at sample point n.

7. The method of claim 1, wherein processing the data to identify the plurality of frequency measurements comprises:
    determining a mean frequency of a windowed signal of an ultrasonic A-scan of the number of ultrasonic A-scans using an autocorrelation function of a complex, analytic representation of the windowed signal of the ultrasonic A-Scan, $\hat{R}(t)$, according to at least one of equation $$f_{mean} = \frac{1}{2\pi i} \frac{\dot{R}(0)}{R(0)} = \frac{1}{2\pi} \dot{\phi}(0),$$

where R(0) is the magnitude of complex autocorrelation function, $\hat{R}(t)$, at time zero, and Ø(0) is the phase of the complex autocorrelation function at the time zero, and a dot above a function represents a time derivative of that function, or for an N-point sampled version of the A-Scan, $$f_{mean} = \tan^{-1}\left[\frac{\mathrm{im}R_N(1)}{\mathrm{re}R_N(1)}\right],$$

where $R_N(1)$ is the N-point complex autocorrelation function $R_N$ evaluated at sample point 1, im refers to the imaginary part of the complex autocorrelation function and re refers to the real part of the complex autocorrelation function.

8. The method of claim 1, wherein the wide-band ultrasonic signals are detected using a point-like optical detector.

9. A method of non-destructive inspection capable of detecting inconsistencies previously masked by a structure signal, the method comprising:
directing a pulsed laser beam towards a composite structure comprised of a plurality of layers, wherein a number of wide-band ultrasonic signals are formed in the composite structure when radiation of the pulsed laser beam is absorbed by the composite structure;
detecting the wide-band ultrasonic signals to form data, wherein the data comprises a plurality of ultrasonic A-scans for the composite structure;
applying a moving window to each of the plurality of ultrasonic A-scans to form windowed signals, wherein the moving window is a filter;
determining a frequency measurement within the windowed signals for each of the plurality of ultrasonic A-scans;
removing spectral components of a structure signal from an A-scan spectrum of each of the plurality of ultrasonic A-scans using the frequency measurement;
performing an interpolation on the A-scan spectrum of the each of the plurality of ultrasonic A-scans after removing the spectral components of the structure signal to form interpolated A-scan spectrum data; and
determining whether an inconsistency is present in the composite structure based on the interpolated A-scan spectrum data.

10. The method of claim 9 further comprising:
Fourier transforming each of the plurality of ultrasonic A-scans to form the A-scan spectrum of each of the plurality of ultrasonic A-scans; and
performing an inverse Fourier transformation on the interpolated A-scan spectrum data to form a plurality of structureless ultrasonic A-scans.

11. The method of claim 10 further comprising:
filtering a structureless B-scan image formed from the plurality of structureless ultrasonic A-scans, wherein determining whether an inconsistency is present in the composite structure based on the interpolated A-scan spectrum data comprises analyzing the structureless B-scan image for an inconsistency.

12. The method of claim 11, wherein filtering the structureless B-scan image comprises using a low-pass filter on the structureless B-scan image.

13. The method of claim 9, wherein the frequency measurement is selected from a mean frequency or a maximum frequency.

14. The method of claim 13, wherein the mean frequency is determined using an autocorrelation function of a complex, analytic representation of a windowed signal of an ultrasonic A-Scan, $\hat{R}(t)$, according to at least one of the equation $$f_{mean} = \frac{1}{2\pi i} \frac{\dot{R}(0)}{R(0)} = \frac{1}{2\pi} \dot{\phi}(0),$$

where R(0) is a magnitude of complex autocorrelation function, $\hat{R}(t)$, at time zero, and Ø(0) is the phase of the complex autocorrelation function at the time zero, and a dot above a function represents the time derivative of that function, or for an N-point sampled version of the A-Scan, according to the equation $$f_{mean} = \tan^{-1}\left[\frac{\mathrm{im}R_N(1)}{\mathrm{re}R_N(1)}\right],$$

where $R_N(1)$ is the N-point complex autocorrelation function $R_N$ evaluated at sample point 1, im refers to the imaginary part of the complex autocorrelation function and re refers to the real part of the complex autocorrelation function.

15. The method of claim 13, wherein the maximum frequency is determined using equation $S_n = \Sigma_{k=1}^{P} a_k * S_{n-k}$, where p is a quantity of coefficients and $S_n$ is an A-scan signal at sample point n.

16. A method of non-destructive inspection capable of detecting inconsistencies previously masked by a structure signal, the method comprising:
obtaining data for a composite structure using a laser ultrasound inspection system;
determining a width and a frequency of spectral components of the structure signal in the data;
removing the spectral components of the structure signal from the data in a frequency domain;
performing an interpolation routine to fill in a region of an A-scan spectrum left empty by removing the spectral components of the structure signal to form interpolated data; and
performing an inverse Fourier transformation on the interpolated data to form a processed A-scan with the structure signal removed; and
determining whether an inconsistency is present in the composite structure based on the A-scan with the structure signal removed.

17. The method of claim 16 further comprising:
filtering the processed A-scan to form filtered data; and
displaying the filtered data in a structureless B-scan image, wherein determining whether an inconsistency is present in the composite structure based on the A-scan with the structure signal removed comprises analyzing the structureless B-scan image for an inconsistency.

18. The method of claim 16, wherein the frequency of the spectral components of the structure signal is estimated using equation $S_n = \Sigma_{k=1}^{P} a_k * S_{n-k}$, where p is a quantity of coefficients and $S_n$ is an A-scan signal at sample point n.

19. The method of claim 16, wherein the frequency of the spectral components of the structure signal is estimated using an autocorrelation function of a complex, analytic representation of a windowed signal of an ultrasonic A-Scan, $\hat{R}(t)$, according to at least one of equation $$f_{mean} = \frac{1}{2\pi i} \frac{\dot{R}(0)}{R(0)} = \frac{1}{2\pi} \dot{\phi}(0),$$

where $R(0)$ is a magnitude of complex autocorrelation function, $\hat{R}(t)$, at time zero, and $\emptyset(0)$ is the phase of the complex autocorrelation function at the time zero, and a dot above a function represents the time derivative of that function, or for an N-point sampled version of the A-Scan, $$f_{mean} = \tan^{-1}\left[\frac{\operatorname{im}R_N(1)}{\operatorname{re}R_N(1)}\right],$$

where $R_N(1)$ is the N-point complex autocorrelation function $R_N$ evaluated at sample point 1, im refers to the imaginary part of the complex autocorrelation function and re refers to the real part of the complex autocorrelation function.

20. The method of claim 16, wherein a spectral region around the spectral components of the structure signal is a mean frequency±two times a width of a structural signal spectrum in the frequency domain, wherein the width of the structural signal spectrum in the frequency domain is a width of the A-scan spectrum associated with spectral components.

21. The method of claim 20, wherein the width of the structural signal spectrum in the frequency domain is estimated using an autocorrelation function of a complex, analytic representation of the windowed signal of an ultrasonic A-Scan, $\hat{R}(t)$, and wherein for an N-point sampled version of the A-Scan, $$\text{width} = \frac{2}{N}\left[1 - \frac{|R_N(1)|}{R_N(0)}\right],$$

where $|R_N(1)|$ is the magnitude of the N-point complex autocorrelation function $R_N$ evaluated at sample point 1 and $R_N(0)$ is the N-point complex autocorrelation function $R_N$ evaluated at sample point 0.

* * * * *